United States Patent [19]

Webb et al.

[11] Patent Number: 5,514,777
[45] Date of Patent: May 7, 1996

[54] METHODS OF SYNTHESIS OF PEPTIDYL ARGININALS

[75] Inventors: Thomas R. Webb, Encinitas; John E. Reiner, San Diego; Susan Y. Tamura, San Diego; William C. Ripka, San Diego; Raymond Dagnino, Jr., San Diego, all of Calif.

[73] Assignee: Corvas International, Inc., San Diego, Calif.

[21] Appl. No.: 261,380

[22] Filed: Jun. 17, 1994

[51] Int. Cl.$^6$ .............................. C07K 5/00; C07K 7/00; C07K 17/00; C07D 211/22
[52] U.S. Cl. .................. 530/331; 530/324; 530/325; 530/326; 530/327; 530/328; 530/329; 530/330; 530/345; 546/221; 546/243
[58] Field of Search ................................. 530/324–331, 530/345; 546/221, 243

[56] References Cited

U.S. PATENT DOCUMENTS

| | | | |
|---|---|---|---|
| 4,316,889 | 2/1982 | Bajusz et al. | 424/177 |
| 4,703,036 | 10/1987 | Bajusz et al. | 514/18 |
| 5,153,176 | 10/1992 | Abe et al. | 514/18 |

FOREIGN PATENT DOCUMENTS 0526877  2/1993  European Pat. Off. .

OTHER PUBLICATIONS

Bajusz, Sandor, et al., *J. Med. Chem.*, 1990, 33, pp. 1739–1735.

McConnell, Rose, et al., *J. Med. Chem.*, 1990, 36, pp. 1084–1089.

Shuman, Robert T., et al., *J. Med. Chem.*, 1993, 36, pp. 314–319.

*Primary Examiner*—Jill Warden
*Assistant Examiner*—Sheela J. Huff
*Attorney, Agent, or Firm*—Lyon & Lyon

[57] ABSTRACT

This invention provides solution-phase methods for the synthesis of peptidyl argininals and to novel reagents useful therein.

79 Claims, 3 Drawing Sheets

METHODS OF SYNTHESIS OF PEPTIDYL ARGININALS

TECHNICAL FIELD

This invention relates to solution-phase methods for the synthesis of peptidyl argininals and to novel reagents useful therein. Using the disclosed methods and reagents of the present invention, peptidyl argininals can be rapidly and efficiently produced. The peptidyl argininals are useful as enzyme inhibitors, in vitro diagnostic agents and in vivo pharmaceutical agents.

BACKGROUND

The trypsin sub-family of serine proteases (referred to as the trypsin-like serine proteases) is composed of proteases which hydrolyze peptide bonds that follow an arginine or lysine residue. These proteases play an important physiological role in digestion, coagulation, fibrinolysis, blood pressure regulation, fertility, and inflammation. "Design of Enzyme Inhibitors as Drugs", Oxford Science Publications, (Edits. Sandler, M., Smith, H. J. 1989). Selective inhibitors of trypsin-like serine proteases are thought to be useful as drugs for intervention into many disease states in which the involvement of these proteases has been implicated.

Peptide analogs which utilize the catalytic mechanism of an enzyme (e.g. transition-state inhibitors) have been suggested as inhibitors of the trypsin-like serine proteases. The catalytic mechanism of these proteinases is thought to involve the attack of the active-site serine on the carbonyl bearing the scissile amide bond of the substrate, to give a tetrahedral intermediate which subsequently results in peptide bond cleave. It has been reported that peptide analogs which are stable mimics of this tetrahedral intermediate (i.e., transition-state analogs) can be selective enzyme inhibitors. Delbaere, L. T. J., Brayer, G. D., J. Mol. Biol. 183:89–103, 1985 and "Proteases and Biological Control", Cold Spring Harbor Laboratory Press, pp. 429–454 (Edits. Aoyagi, T. and Umezawa, H. 1975). Selective transition-state inhibitors of the trypsin-like serine proteases may therefore be useful as drugs for intervention into many disease states in which the involvement of these proteases has been implicated.

One candidate group of transition-state inhibitors which may be particularly useful are the peptide analogs which have an aldehyde group on the C-terminus of the peptide analog. Peptide aldehydes were initially discovered as natural products produced by a number of actinomycete strains. Some derivatives of natural products have been reported to be selective inhibitors of various types of serine and cysteine proteinases. Aoyagi, T., Supra. For example, the peptide, alaninal elastatinal, was reported to be a potent elastase inhibitor, but not an inhibitor of trypsin or the trypsin-like serine proteases. Hassall, C. H. et al., FEBS Lett., 183:201–205 (1985). Elastase inhibitors are of interest in the treatment of diseases such as emphysema and synthetic peptide aldehydes have been reported to be excellent inhibitors of human leukocyte elastase. Sandler, M., Smith, H. J., Supra. It has been reported that the selectivity of these naturally occurring analogs has been enhanced by modifying the peptide sequence. Bajusz, S. et al., J. Med. Chem. 33:1729–1735 (1990); and McConnell, R. M. et al., J. Med. Chem. 33: 86–93 (1990).

The peptidyl argininal, leupeptin (Acetyl-L-Leu-L-Leu-L-Arg-al), has been reported to be a selective inhibitor of trypsin-like serine proteases. "Structures and activities of protease inhibitors of microbial origin", Proteases and Biological Control, Cold Spring Harbor Laboratory Press, pp. 429–454 (Edits. Aoyagi, T., Umezawa, H. 1975). Leupeptin, along with its naturally occurring variants and synthetic analogs, have been reported to be potent inhibitors of several trypsin-like serine proteases in the coagulation cascade.

The peptide argininal, D-Phe-L-Pro-L-Arg-al, and analogs thereof, have been reported to show a marked selectivity for particular coagulation factors. For example, one such analog (N-methyl-D-Phe-Pro-Arg-al) has been developed as a thrombin inhibitor and is reported to have significant in vivo anticoagulant activity. U.S. Pat. Nos. 4,316,889 (1982), 4,399,065 (1983), 4,478,745 (1984), 4,346,078 (1982), and 4,708,039 (1987).

A major problem in medical research directed to the use of peptidyl aldehydes as potential drugs for intervention into many disease states in which trypsin-like serine proteases have been implicated has been the difficulty in synthesizing the peptidyl argininals. Though solution-phase methods for their synthesis have been reported, their synthesis remains a labor-intensive and time-consuming process.

Three methods for the solution-phase synthesis of peptidyl argininals (Arg-al), each using a different intermediate, have been reported.

The use of L-Leu-L-Arg-al dibutylacetal as an intermediate has been reported in the synthesis of more than 30 peptidyl argininals. In particular, L-Leu-L-Arg-al was reported to be prepared by thermolysin digestion of leupeptin (acetyl-L-Leu-L-Leu-L-Arg-al), transformation of the digestion product to a racemic dibutyl acetal (L-Leu-D,L-Arg-dibutylacetal), followed by separation of the diastereomers. Saino, T et al., Chem. Pharm. Bull., 30(7):2319 (1982); T. Saino et al., J. Antibiotics, 41:220 (1988).

The use of the $N^\omega$-carbobenzyloxy-arginine lactam as an intermediate in the synthesis of peptidyl argininals has been reported. The lactam was reported to be coupled to a variety of peptides in good to high yield. The resulting peptidyl-$N^\omega$-carbobenzyloxy-arginine lactam was reduced with $LiAlH_4$ to form the peptidyl-$N^\omega$-carbobenzyloxy-argininal, and subsequently hydrogenated to give the peptidyl argininal. Basjusz, S. et al, J. Med. Chem., 53: 1729 (1990); Shuman, R. T. et al., J. Med. Chem., 36:314 (1993); Balasubramanian, N. et al., J. Med. Chem., 36:300 (1993).

The use of semicarbazone intermediates has been reported in the synthesis of peptidyl argininals. The unsubstituted semicarbazone, $N^g$-nitro-L-argininal semicarbazone, was used as an intermediate in the synthesis of peptidyl argininals. McConnell, R. M. et al., J. Med Chem., 33:86 (1990); R. M. McConnell, J. L. York, D. Frizzell, C, Ezell, J. Med Chem., 36, 1084–1089 (1993). $N^g$-nitro-L-argininal semicarbazonyl-4-methylcyclohexane carboxylic acid was reported as an intermediate in the preparation of peptide aldehydes by a solid phase method. Murphy, A. M. et al., J. Am. Chem. Soc., 114:3156 (1992); and Webb, T. R., U.S. Pat. No. 5,283,293 (Feb. 1, 1994). $N^g$-nitro-L-argininal semicarbazonyl-4-diphenylmethane was reported as an intermediate for the solution-phase synthesis of peptidyl argininals. Brunck, T. K. et al., WO 93/14779 (1993).

SUMMARY OF THE INVENTION

In one aspect, the present invention is directed to novel compounds useful for the solution-phase synthesis of peptidyl argininals. These compounds have the formula:

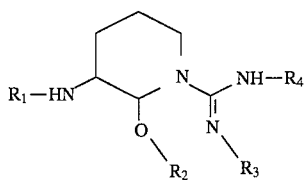

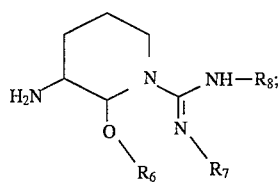

wherein

R₁ is selected from the group consisting of hydrogen, benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

R₂ is selected from the group consisting of alkyl of 1 to about 12 carbon atoms, aralkyl of about 7 to about 15 carbon atoms, and alkyl of about 2 to about 12 carbon atoms substituted with a hydroxy, carbomethoxy or carboethoxy;

R³ is selected from the group consisting of nitro, benzyloxycarbonyl, t-butoxycarbonyl and adamantyloxycarbonyl; and R₄ is selected from the group consisting of hydrogen, alkyl of 1 to about 12 carbon atoms, aryl of about 6 to about 14 carbon atoms and aralkyl of about 7 to about 15 carbon atoms; and salts thereof.

In another aspect, the present invention is directed to salts of the compounds of the present invention.

In yet another aspect, the present invention is directed to methods of preparing peptidyl argininals, which comprises:

(a) reacting a first intermediate having the formula:

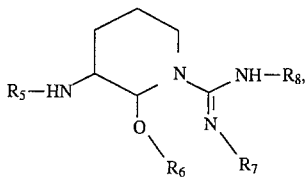

wherein

R₅ is selected from the group consisting of benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

R₆ is selected from the group consisting of alkyl of 1 to about 12 carbon atoms, aralkyl of about 7 to about 15 carbon atoms, and alkyl of 2 to about 12 carbon atoms substituted with a hydroxy, carbomethoxy or carboethoxy;

R7 is selected from the group consisting of nitro, benzyloxycarbonyl, t-butoxycarbonyl and adamantyloxycarbonyl; and R₈ is selected from the group consisting of hydrogen, alkyl of 1 to about 12 carbon atoms, aryl of about 6 to about 14 carbon atoms, and aralkyl of about 7 to about 15 carbon atoms; with a R₅ removing reagent which chemically removes the R₅ group from said first intermediate to give a second intermediate of the formula:

(b) chemically coupling to the second intermediate of step (a), a protected amino acid, a protected amino acid analog or a protected peptide of about 2 to about 30 amino acids, amino acid analogs, or a combination of amino acids and amino acid analogs, using a coupling reagent to give a third intermediate having the formula:

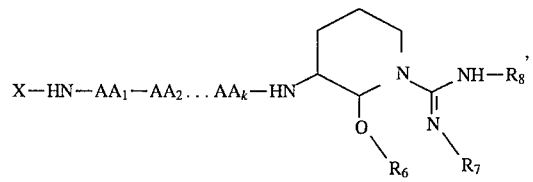

wherein

X is a protecting group, k is an integer from 1 to 30, and

AA₁-AA₂ ... AA_k is an amino acid, amino acid analog or peptide comprised of k amino acids, amino acid analogs or a combination of amino acids and amino acid analogs;

(c) reacting the third intermediate with a R₇ removing reagent which chemically removes the R₇ group to give a fourth intermediate having the formula:

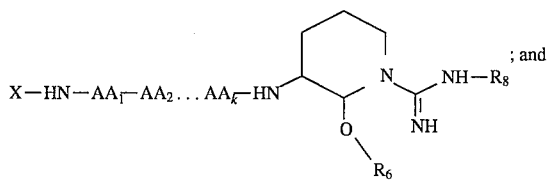

(d) reacting the fourth intermediate with a hydrolyzing reagent which comprises an aqueous acid to chemically hydrolyze said fourth intermediate to give said peptidyl argininal.

Thus, provided are methods of making peptidyl argininals comprising the steps of:

(a) preparing a first intermediate having the formula:

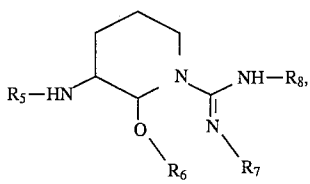

wherein

R₅ is selected from the group consisting of benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

R6 is selected from the group consisting of alkyl of 1 to about 12 carbon atoms, aralkyl of about 7 to about 15 carbon atoms, and alkyl of 2 to about 12 carbon atoms substituted with a hydroxy, carbomethoxy or carboethoxy;

R7 is selected from the group consisting of nitro, benzyloxycarbonyl, t-butoxycarbonyl and adamantyloxycarbonyl; and R8 is selected from the group consisting of hydrogen, alkyl of 1 to about 12 carbon atoms, aryl of about 6 to about 14 carbon atoms, and aralkyl of about 7 to about 15 carbon atoms;

(b) chemically removing the R5 group from said first intermediate to give a second intermediate;

(c) chemically coupling to said second intermediate having its R5 group removed, a protected amino acid, protected amino acid analog or protected peptide comprised of about 2 to about 30 amino acids, amino acid analogs, or a combination of amino acids and amino acid analogs, to give a third intermediate having the formula:

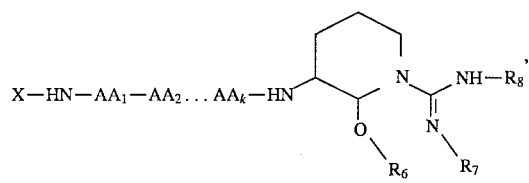

wherein

X is a protecting group, k is an integer from 1 to 30, and $AA_1$-$AA_2$...$AA_k$ is an amino acid, amino acid analog or peptide comprised of k amino acids, amino acid analogs or a combination of amino acids and amino acid analogs;

(d) chemically removing the $R_7$ group from said third intermediate to give a fourth intermediate having the formula:

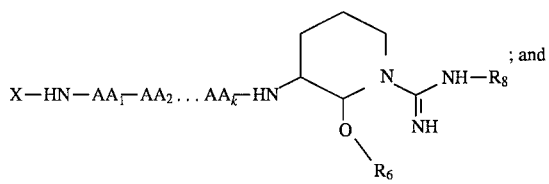

(e) chemically hydrolyzing said fourth intermediate in a liquid comprising an aqueous acid.

In yet another aspect, the present invention is directed to peptidyl argininals made by the disclosed methods.

Definitions.

In accordance with the present invention and as used herein, the following terms are defined to have the following meanings, unless explicitly stated otherwise.

The term "alkyl" refers to saturated aliphatic groups including straight-chain, branched-chain and cyclic groups.

The term "alkoxy" refers to a group having the formula, R—O—, wherein R is an alkyl group.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkyl" refers to an alkyl group substituted with an aryl group. Suitable aralkyl groups include benzyl, picolyl, and the like, all of which may be optionally substituted.

The term "aralkoxy" refers to a group having the formula, R—O—, wherein R is an aralkyl group.

The term "amino acid" refers to both natural, unnatural amino acids in their D and L stereoisomers, and their analogs, if their structures allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Set), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein the N-terminal amino group, C-terminal carboxy group or side chain group has been chemically blocked or modified to another functional group.

The term "amino acid residue" refers to radicals having the structure: (1) —HN—R—C(O)—, wherein R typically is —CH(R')—, wherein R' is H or a carbon containing

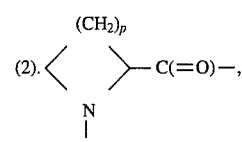

substituent; or wherein p is 1, 2 or 3 representing the azetidinecarboxylic acid, proline or pipecolic acid residues, respectively.

The term "L-argininal" refers to L-arginine in which the carboxy group has been replaced with an aldehyde group. L-argininal has the formula:

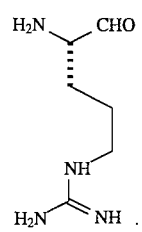

The term "D-argininal" refers to D-arginine in which the carboxy group has been replaced with an aldehyde group. D-argininal has the formula:

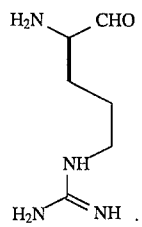

The term "non-adverse conditions" describes conditions of reaction or synthesis which do not substantially adversely affect the skeleton of the peptide analog and/or its amino acid (and/or amino acid analog) components. One skilled in the art can readily identify functionalities, coupling procedures, deprotection procedures and cleavage conditions which meet these criteria.

The term "peptide" refers to oligomers of amino acids which are linked by peptide bonds. The nomenclature used to define the peptides is that specified by Schroder & Lubke, "The Peptides," Academic Press (1965), wherein in accordance with conventional representation the amino group at the N-terminus appears to the left and the carboxyl group at the C-terminus to the right.

The term "peptidyl argininal" refers to a peptide in which the C-terminal amino acid is either L-argininal or D-argininal.

In addition, the following abbreviations stand for the following: "N-Boc-$N^g$-nitro-L-arginine" refers to the compound which has the formula:

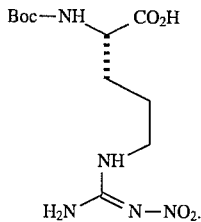

"L-Arg-al" refers to L-argininal.

"D-Arg-al" refers to D-argininal.

"Boc" refers to t-butoxycarbonyl.

"BOP" refers to benzotriazol-1-yloxy-tris(dimethylamino)-phosphonium-hexafluorophosphate.

"Brine" means an aqueous saturated solution of sodium chloride.

"DCC" refers to 1,3-dicyclohexylcarbodiimide.

"EDC" refers to ethyl-3-(3-dimethylamino)propylcarbodiimide hydrochloride salt.

"HBTU" refers to 2-(1H-benzotriazol-1-yl)-1,1,3,3-tetramethyluronium hexafluorophosphate.

"HCl" refers to hydrochloric acid.

"HF" refers to hydrofluoric acid.

"HOBt" refers to 1-hydroxybenzotriazole monohydrate.

"2-PrPen" refers to 2-propylpentanoyl.

"LiAlH$_4$" refers to lithium aluminum hydride.

"LiAlH$_2$(OEt)$_2$ refers to lithium aluminum dihydride diethoxide.

"TBTU" refers to 2-(1H-benzotriazol-1-yl)-1,1,3,3-tetramethyluronium tetrafluoroborate.

DETAILED DESCRIPTION OF THE INVENTION

Figure 1:
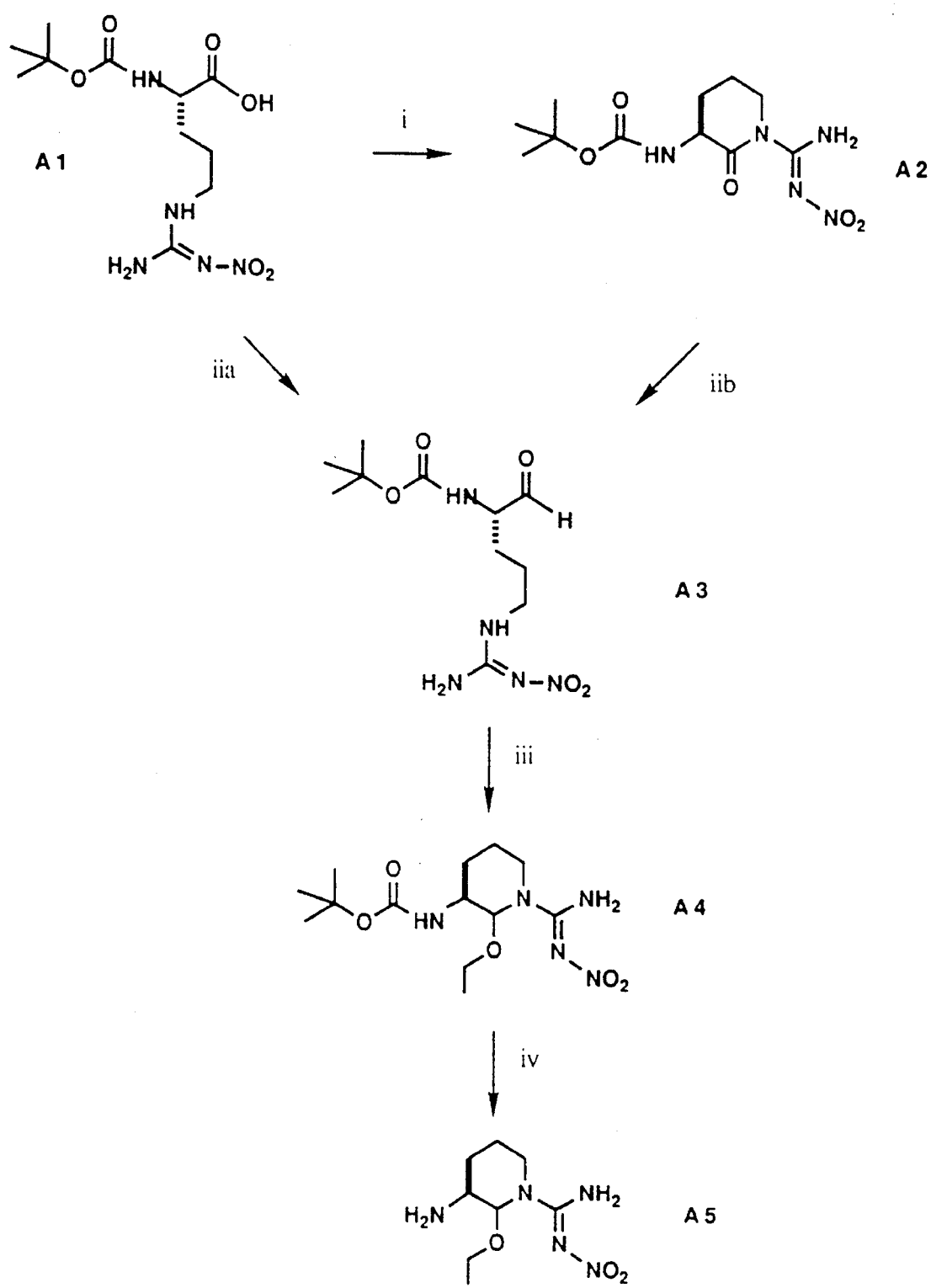
FIG. 1 depicts the reaction scheme for preparation of a compound of the present invention, $N^g$-nitro-L-argininal ethyl cyclol. In this figure, (i)–(iv) are defined as: i) isobutyl chloroformate, 1-methylpiperidine, tetrahydrofuran; iia) isobutyl chloroformate, 1-methylpiperidine, O,N-dimethylhydroxylamine, HCl salt, tetrahydrofuran; LiAlH$_4$, tetrahydrofuran; IIb) LiAlH$_2$(OCH$_2$CH$_3$)$_2$, tetrahydrofuran; iii) concentrated HCl, ethanol; and iv) anhydrous acid, ethanol.

1. Preferred Compounds.

In one aspect, the present invention is directed to compounds which are useful as intermediates for the synthesis of peptidyl aldehydes. These compounds have the formula:

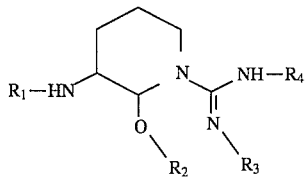

(I)

The preferred compounds of the present invention include those wherein R$_4$ is hydrogen or alkyl of 1 to about 12 carbon atoms. Suitable alkyls for R$_4$ include methyl, ethyl, 1-propyl, 2-methyl-1-propyl, 2,2-dimethyl-1-propyl, 2-propyl, 2-methyl-2-propyl, 1-butyl, 2-butyl, 3-butyl, 3-methyl-1-butyl, 1-pentyl, cyclopentyl, 1-hexyl, cyclopentylmethyl, cyclohexyl, cyclohexylmethyl, 1-heptyl, 4-heptyl, octyl, nonanyl, dodecanyl, adamantyl or adamantylmethyl. Especially preferred compounds include those wherein R4 is hydrogen, methyl, ethyl or propyl. More especially preferred compounds include those wherein R$_4$ is hydrogen.

The preferred compounds of the present invention include those wherein R$_3$ is nitro, benzyloxycarbonyl, t-butoxycarbonyl, adamantyloxycarbonyl, 2,2,5,7,8-pentamethylchroman-6-sulfonyl, 4-methoxy-2,3,6-trimethylbenzenesulfonyl and 4-methylbenzenesulfonyl.

In one aspect, the preferred compounds of the present invention include those wherein R$_3$ is nitro or benzyloxycarbonyl. In this case, the preferred compounds include those wherein R$_1$ is hydrogen, t-butoxycarbonyl, t-amyloxycarbonyl, isobornyloxycarbonyl, adamantyloxycarbonyl, 4-methoxybenzyloxycarbonyl, or 2-(4-biphenyl)-2-propyloxycarbonyl. More especially preferred compounds include those wherein R$_1$ is hydrogen or t-butoxycarbonyl. Especially preferred compounds include those wherein R$_3$ is nitro and R$_1$ is hydrogen or t-butoxycarbonyl.

In another aspect, the preferred compounds of the present invention include those wherein R$_3$ is t-butoxycarbonyl or adamantyloxycarbonyl. In this case, the preferred compounds include those wherein R$_1$ is hydrogen, benzyloxycarbonyl, isonicotinyloxycarbonyl, 2-chlorobenzyloxycarbonyl, 9-fluorenylmethoxycarbonyl or methylsulfonylethoxycarbonyl. Especially preferred compounds include wherein $R_1$ is hydrogen or benzyloxycarbonyl. More especially preferred compounds include those wherein $R_3$ is t-butoxycarbonyl and $R_1$ is hydrogen or benzyloxycarbonyl.

The preferred compounds of the present invention include those wherein $R_2$ is alkyl of 1 to about 12 carbon atoms. Suitable alkyls for $R_2$ include methyl, ethyl, 1-propyl, 2-methyl-1-propyl, 2,2-dimethyl-1-propyl, 2-propyl, 2-methyl-2-propyl, 1-butyl, 2-butyl, 3-butyl, 3-methy-1-butyl, 1-pentyl, cyclopentyl, 1-hexyl, cyclopentylmethyl, cyclohexyl, cyclohexylmethyl, 1-heptyl, 4-heptyl, octyl, nonanyl, dodecanyl, adamantyl or adamantylmethyl. Especially preferred compounds include those wherein $R_2$ is methyl, ethyl, propyl or isopropyl. More especially preferred compounds include those wherein $R_2$ is ethyl.

Certain preferred compounds of the present invention include:

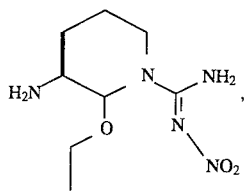

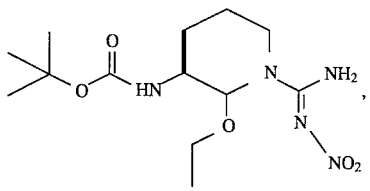

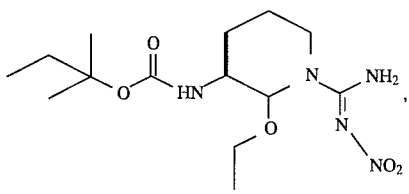

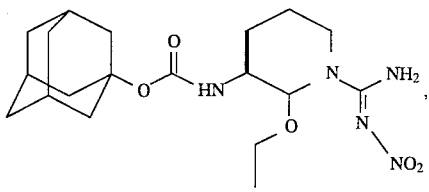

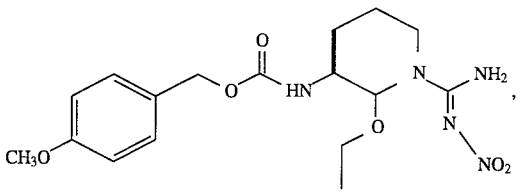

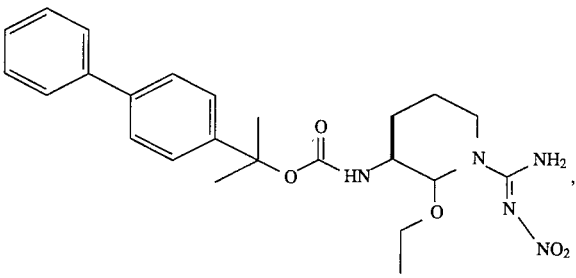

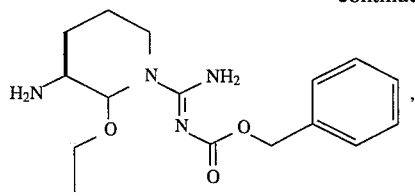,
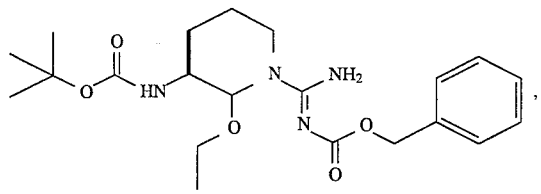,
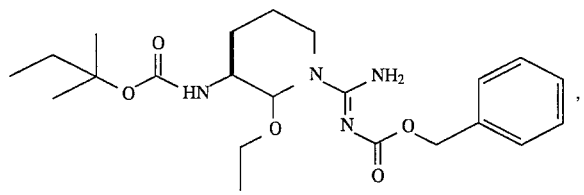,
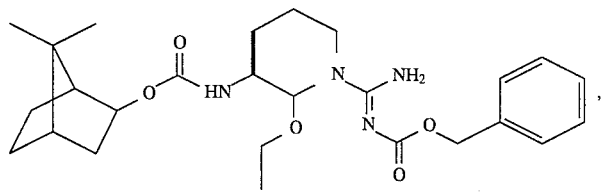,
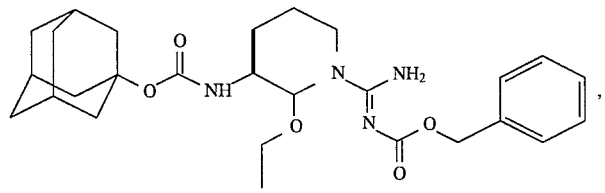,
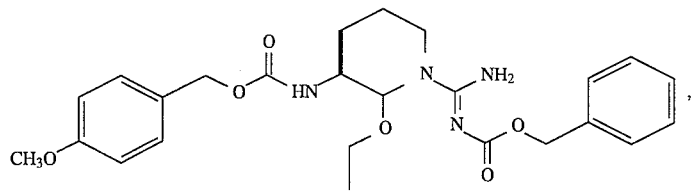,
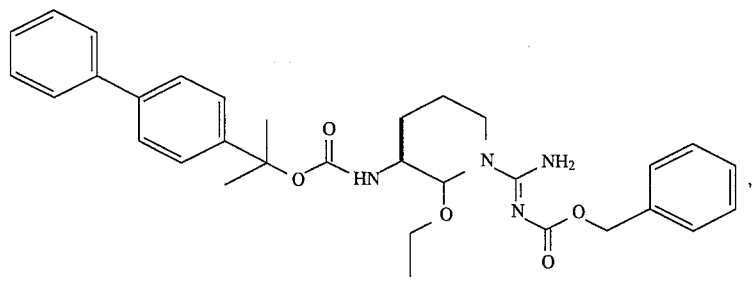,
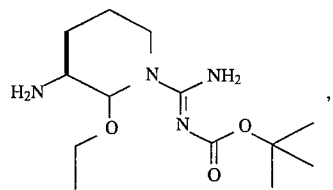,

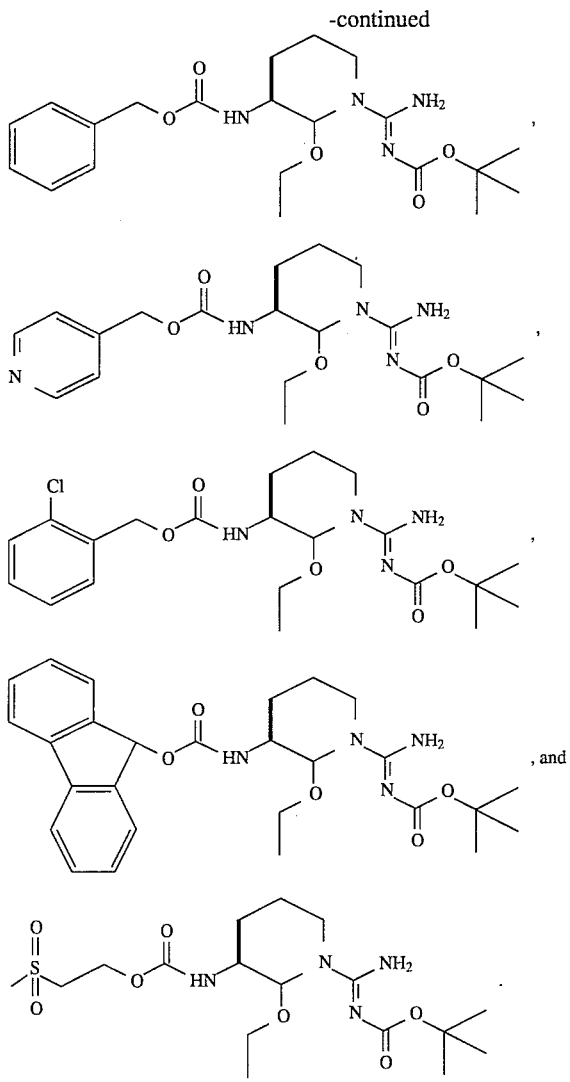

In another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, acetic acid, trifluoroacetic acid and other suitable acid addition salts.

2. Preparation of Preferred Compounds.

The compounds of the present invention are synthesized by solution-phase methods.

Many of the starting materials used in the syntheses are readily available from chemical vendors such as Aldrich, Sigma, Nova Biochemicals, Bachem Biosciences, Inc. and the like.

FIG. 1 illustrates preferred routes for the synthesis of the compounds of the present invention, N-alpha-t-butoxycarbonyl-N $^g$-nitro-L-argininal ethyl cyclol and N$^g$-nitro-L-argininal ethyl cyclol. The latter may be prepared either as its trifluoroacetate or hydrochloride salt. Further details for the synthesis of these compounds are disclosed in Example 1 through 5.

Figure 2:
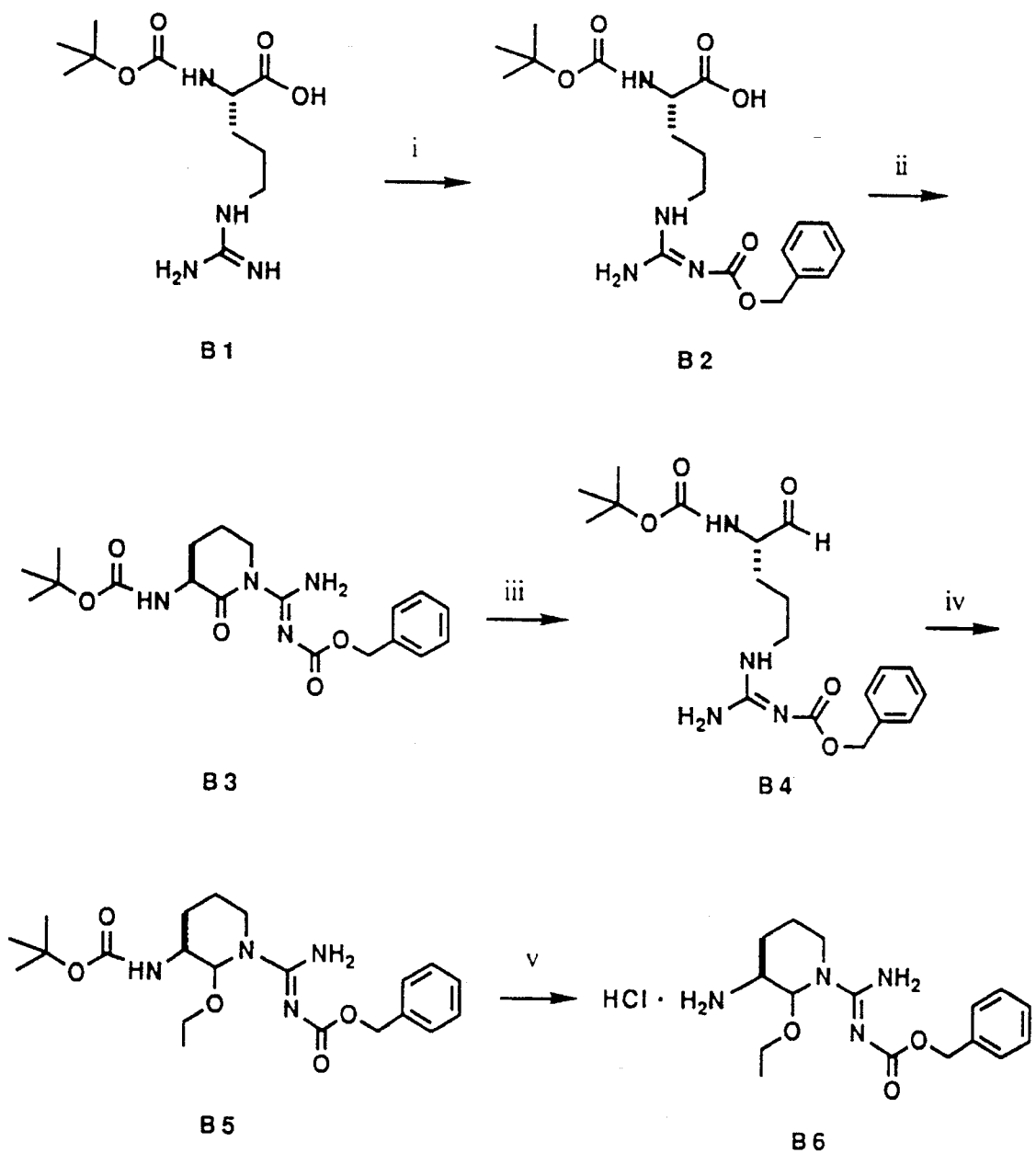
FIG. 2 depicts the reaction scheme for preparation of a compound of the present invention, $N^g$-benzyloxycarbonyl-L-argininal ethyl cyclol. In this figure, (i)–(v) are defined as: i) benzyl chloroformate, aqueous sodium hydroxide; ii) isobutyl chloroformate, N-methylmorpholine, triethylamine, tetrahydrofuran; iii) LiAlH$_4$, tetrahydrofuran; iv) concentrated HCl, ethanol; v) anhydrous HCl, ethanol.

FIG. 2 illustrates a preferred route for the synthesis of two more of the compounds of the present invention, N-alpha-t-butoxycarbonyl-N$^g$-benzyloxycarbonyl-L-argininal ethyl cyclol and N$^g$-benzyloxycarbonyl-L-argininal ethyl cyclol. The latter may be prepared as its hydrochloride salt. Further details for the synthesis of these compounds are dislosed in Example 24 through 29.

As exemplified in FIGS. 1 and 2, certain protected argininals (A3 of FIG. 1 and B4 of FIG. 2) may be converted to the compounds of the present invention by cyclization. FIG. 1 provides a preferred reaction scheme for cyclization of A3 to give A4. Likewise, FIG. 2 provides a preferred reaction scheme for cyclization of B4 to give B5.

The compounds of formula (I) may be prepared by cyclization of certain protected argininals (as for example, A3 or B4) by means of treating them in a liquid mixture comprised of an acid and alcohol. Preferred means include treatment in a liquid mixture comprised of HCl and alcohol, p-toluenesulfonic acid and alcohol, pyrdinium p-toluenesulfonate and alcohol, and camphorsulfonic acid and alcohol. Especially preferred means include treatment in a liquid mixture comprised of concentrated HCl and an alcohol at 0°–30° C., more preferably at 20°–25° C.

Where methyl is desired as $R_2$, more especially preferred means include treatment in concentrated HCl in absolute methanol at 0°–30° C., preferably at 20°–25° C. Where ethyl is desired as $R_2$, more especially preferred means include treatment in concentrated HCl in absolute ethanol at 0°–30° C., preferably at 20°–25° C. Where n-propyl is desired as $R_2$, more especially preferred means include treatment in concentrated HCl in n-propanol at 0°–30° C., preferably at 20°–25° C. Where isopropyl is desired as $R_2$, more especially preferred means include treatment with concentrated HCl in isopropanol at 0°–30° C., preferably at 20°–25° C.

3. Utility.

The compounds and methods of the present invention are useful for making peptidyl argininals. Certain peptidyl argininals are useful as enzyme inhibitors or in vitro diagnostic reagents. For example, the peptidyl argininals described in Example 11 (2-PrPen-Asp(OCH$_3$)-Pro-Arg-al) and Example 14 (2-PrPen-Asp-Pro-Arg-al) herein have been reported to be thrombin inhibitors, as well as, inhibitors of blood clotting. Vlasuk et al., WO 93/15756 (Aug. 19, 1993). Thus, certain peptidyl argininals (such as those of Examples 11 and 14) made by using the compounds and methods of the present invention are useful as additives to solutions to inhibit the enzyme activity of thrombin.

The use of anticoagulants as in vitro diagnostic reagents is well known. For example, the use of stoppered test tubes containing anticoagulants and having a vacuum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such tubes contain clot-inhibiting additives (such as heparin salts, EDTA salts, citrate salts or oxalate salts), and are useful for the isolation of mammalian plasma from the blood. As potent inhibitors of blood clotting, certain peptidyl argininals (such as those described in Examples 11 and 14 of this application) are also useful as in vitro diagnostic reagents for addition into blood collection tubes.

4. Methods

Figure 3:
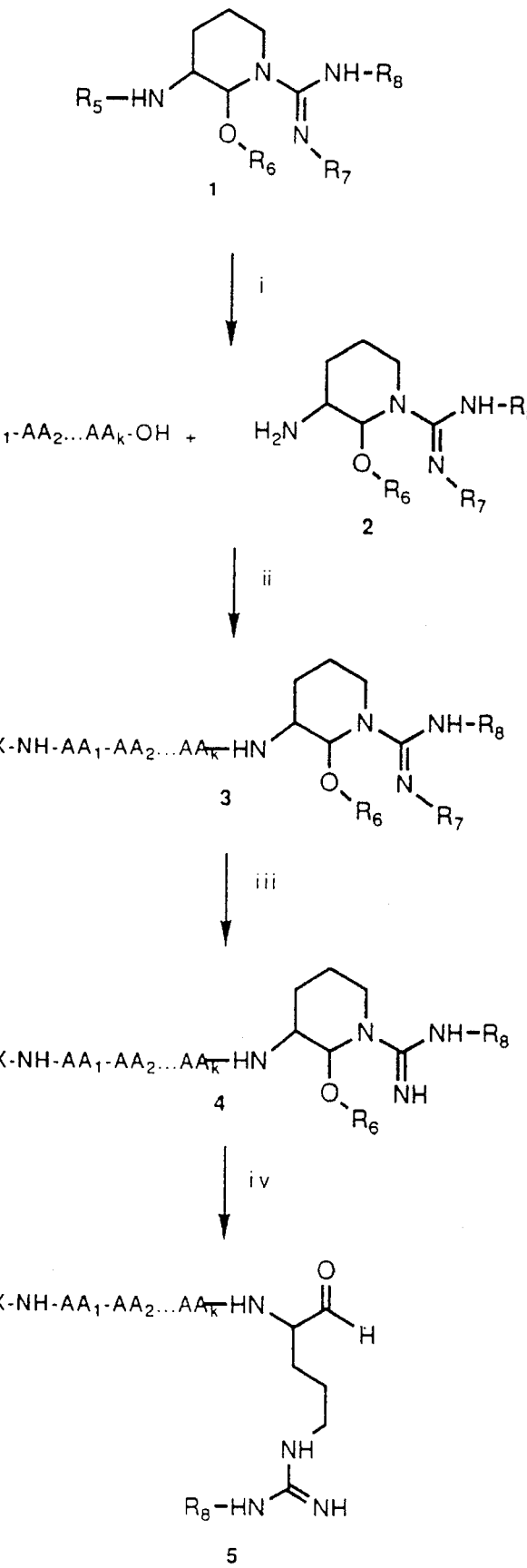
FIG. 3 depicts a method of making peptidyl argininals using the compounds of the present invention. In this figure, (i)–(iv) are defined as: i) trifluoroacetic acid in dichloromethane or anhydrous HCl in absolute ethanol; ii) HBTU, HOBt, N-methylmorpholine, acetonitrile; iii) H$_2$, 10% palladium on carbon, ethanol, acetic acid, water; iv) HPF$_6$, aqueous acetonitrile.

In another aspect, the present invention is directed to methods of making peptidyl argininals. FIG. 3 depicts the reaction scheme for a preferred method of the present invention. Exemplars of this reaction scheme disclosed in Examples 9–11 and 21–23.

The preferred methods of the present invention include those comprising the steps of:

(a) preparing a first intermediate having the formula:

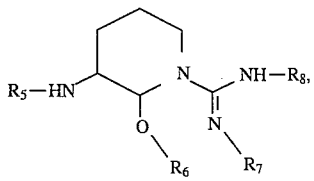

wherein $R_5$ is selected from the group consisting of benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

$R_6$ is selected from the group consisting of alkyl of 1 to about 12 carbon atoms, aralkyl of about 7 to about 15 carbon atoms, and alkyl of 2 to about 12 carbon atoms substituted with a hydroxy, carbomethoxy or carboethoxy;

$R_7$ is selected from the group consisting of nitro, benzyloxycarbonyl, t-butoxycarbonyl and adamantyloxycarbonyl; and $R_8$ is selected from the group consisting of hydrogen, alkyl of 1 to about 12 carbon atoms, aryl of about 6 to about 14 carbon atoms, and aralkyl of about 7 to about 15 carbon atoms;

(b) chemically removing the $R_5$ group from said first intermediate;

(c) chemically coupling to said first intermediate having its $R_5$ group removed, a protected amino acid, protected amino acid analog or protected peptide comprised of about 2 to about 30 amino acids, amino acid analogs, or a combination of amino acids and amino acid analogs, to give a third intermediate having the formula:

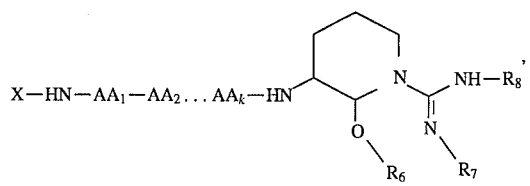

wherein

X is a protecting group, k is an integer from 1 to 30, and $AA_1$-$AA_2$...$AA_k$ is an amino acid, amino acid analog or peptide comprised of k amino acids, amino acid analogs or combination of amino acids and amino acid analogs;

(d) chemically removing the $R_7$ group from said third intermediate to give a fourth intermediate having the formula:

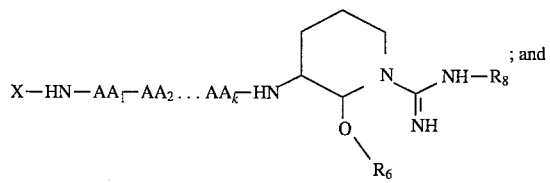

(e) chemically hydrolyzing said fourth intermediate in a liquid comprising an aqueous acid.

As used herein, the term "peptidyl argininal" refers to a peptide in which the C-terminal amino acid is either L-argininal or D-argininal. The term "peptide" refers to to oligomers of amino acids which are linked by peptide bonds. According to the conventional representation, the amino group at the N-terminus appears to the left and the carboxyl group at the C-terminus to the right.

a. Preparing Intermediate.

The preferred first intermediates (as shown above and as formula 1 in FIG. 3) used in the method of the present invention are prepared as described above.

Preferred first intermediates include those wherein $R_8$ is hydrogen or alkyl of 1 to about 12 carbon atoms. Suitable alkyls for $R_8$ include methyl, ethyl, 1-propyl, 2-methyl-1-propyl, 2,2-dimethyl-1-propyl, 2-propyl, 2-methyl-2-propyl, 1-butyl, 2-butyl, 3-butyl, 3-methyl-1-butyl, 1-pentyl, cyclopentyl, 1-hexyl, cyclopentylmethyl, cyclohexyl, cyclohexylmethyl, 1-heptyl, 4-heptyl, octyl, nonanyl, dodecanyl, adamantyl or adamantylmethyl. Especially preferred compounds include those wherein $R_8$ is hydrogen, methyl, ethyl or propyl. More especially preferred compounds include those wherein $R_8$ is hydrogen.

Preferred first intermediates include those wherein $R_7$ is nitro or benzyloxycarbonyl. In this case, preferred compounds include those wherein $R_5$ is t-butoxycarbonyl, t-amyloxycarbonyl, isobornyloxycarbonyl, adamantyloxycarbonyl, 4-methoxybenzyloxycarbonyl, or 2-(4-biphenyl)-2-propyloxycarbonyl. Especially preferred first intermediates include those wherein $R_5$ is t-butoxycarbonyl. More especially preferred first intermediates include those wherein $R_3$ is nitro and $R_1$ is t-butoxycarbonyl.

Alternatively, preferred first intermediates include those wherein $R_7$ is t-butoxycarbonyl or adamantyloxycarbonyl. In this case, the preferred first intermediates include those wherein $R_5$ is benzyloxycarbonyl, isonicotinyloxycarbonyl, 2-chlorobenzyloxycarbonyl, 9-fluorenylmethoxycarbonyl or methylsulfonylethoxycarbonyl. Especially preferred first intermediates include wherein $R_5$ is benzyloxycarbonyl. More especially preferred first intermediates include those wherein $R_7$ is t-butoxycarbonyl and $R_5$ is benzyloxycarbonyl.

The preferred first intermediates include those wherein $R_6$ is alkyl of 1 to about 12 carbon atoms. Suitable alkyls for $R_6$ include methyl, ethyl, 1-propyl, 2-methyl-1-propyl, 2,2-dimethyl-1-propyl, 2-propyl, 2-methyl-2-propyl, 1-butyl, 2-butyl, 3-butyl, 3-methy-1-butyl, 1-pentyl, cyclopentyl, 1-hexyl, cyclopentylmethyl, cyclohexyl, cyclohexylmethyl, 1-heptyl, 4-heptyl, octyl, nonanyl, dodecanyl, adamantyl or adamantylmethyl. Especially preferred first intermediates include those wherein $R_2$ is methyl, ethyl, propyl or isopropyl. More especially preferred first intermediates include those wherein $R_2$ is ethyl.

Certain especially preferred first intermediates include those having the formula:

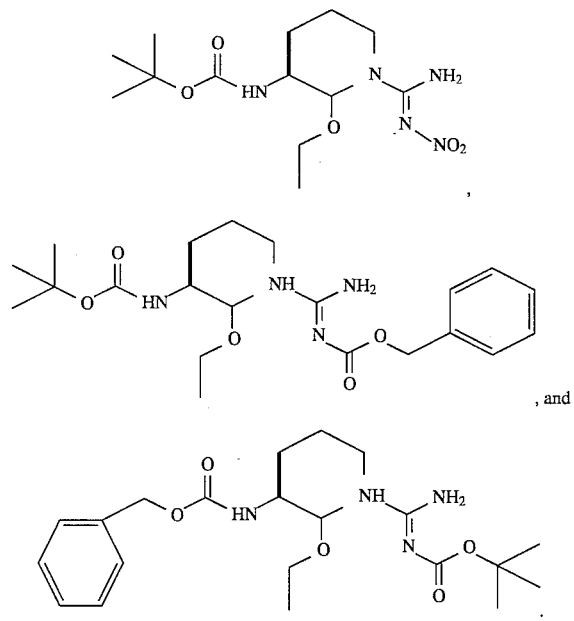

b. Chemically removing $R_5$ group.

As depicted in FIG. 3, the $R_5$ group of the first intermediate 1 is chemically removed to give third intermediate 2.

Where $R_5$ is t-butoxycarbonyl, t-amyloxycarbonyl, isobornyloxycarbonyl, adamantyloxycarbonyl, 4-methoxybenzyloxycarbonyl or 2-(4-biphenyl)-2-propyloxycarbonyl, the preferred means of chemically removing the $R_5$ group from such first intermediates include their treatment with a liquid mixture comprised of an acid and solvent. For example, preferred means include chemically removing such $R_5$ group by treatment with HCl in alcohol, trifluoroacetic acid in a chlorinated hydrocarbon solvent, HCl in acetic acid, HCl in ethereal solvents, HCl in ethyl acetate or methyl acetate, p-toluenesulfonic acid in toluene. Especially preferred means of chemically removing the $R_5$ group include treatment with trifluoroacetic acid in dichloromethane at 0°–30° C., more preferably at 20°–25° C. Where $R_6$ is methyl, another more especially preferred means of chemically removing the $R_5$ group include treatment with HCl in absolute methanol at 0°–10° C., preferably at 0°–5° C. Where $R_6$ is ethyl, another more especially preferred means of chemically removing the $R_5$ group include treatment with HCl in absolute ethanol at 0°–10° C., preferably at 0°–5° C. Where $R_6$ is n-propyl, another more especially preferred means of chemically removing the $R_5$ group include treatment with HCl in n-propanol at 0°–10° C., preferably at 0°–5° C. Where $R_6$ is isopropyl, another more especially preferred means of chemically removing the $R_5$ group include treatment with HCl in isopropanol at 0°–10° C., preferably at 0°–5° C.

Alternatively, where $R_5$ is benzyloxycarbonyl, isonicotinyloxycarbonyl or 2-chlorobenzyloxycarbonyl, the preferred means of chemically removing the $R_5$ group of such first intermediates include their treatment with hydrogen gas, or a source of hydrogen gas, in a liquid mixture comprised of catalyst and solvent. For example, the preferred means of chemically removing such $R_5$ groups include treatment with hydrogen gas and platinum or palladium in a liquid mixture comprised of alcohol, with 1,4-cyclohexadiene and platinum or palladium in a liquid mixture comprised of alcohol, or with ammonium formate and platinum or palladium in a liquid mixture comprised of aqueous acetic acid. The more preferred means of chemically removing $R_5$ groups include their treatment with hydrogen gas and palladium in a liquid mixture comprised of alcohol and acid. Where $R_6$ is methyl, another more especially preferred means of chemically removing $R_5$ groups include treatment with hydrogen gas and 10% palladium on carbon in a liquid mixture comprised of methanol and HCl. Where $R_6$ is ethyl, another more especially preferred means of chemically removing $R_5$ groups include treatment with hydrogen gas and 10% palladium on carbon in a liquid mixture comprised of ethanol and HCl. Where $R_6$ is n-propyl, another more especially preferred means of chemically removing $R_5$ groups include treatment with hydrogen gas and 10% palladium on carbon in a liquid mixture comprised of n-propanol and HCl. Where $R_6$ is isopropyl, another more especially preferred means of chemically removing $R_5$ groups include treatment hydrogen gas and 10% palladium on carbon in a liquid mixture comprised of isopropanol and HCl.

c. Chemically Coupling.

As depicted in FIG. 3, X-HN-AA$_1$-AA$_2$ . . . AA$_k$-OH is coupled to 2 to give a third intermediate 3.

X-HN-AA$_1$-AA$_2$ . . . AA$_k$-OH represents a protected amino acid, protected amino acid analog or protected peptide comprised of amino acids, amino acid analogs or combination of amino acids and amino acid analogs, wherein X-HN-AA$_1$-AA$_2$ . . . AA$_k$-OH has a free C-terminal carboxy group, and "k" is an integer, which is the number of amino acids, amino acid analogs, or the combination of amino acids and amino acid analogs which comprise X-HN-AA$_1$-AA$_2$ . . . AA$_k$-OH. Where "k" is 1, X-HN-AA$_1$-OH is a protected amino acid or protected amino acid analog. Where "k" is 2 to 20, X-HN-AA$_1$-AA$_2$ . . . AA$_k$-OH is a protected peptide comprised amino acids, amino acid analogs, or amino acids and amino acid analogs, the total number of which equals "k". Preferred X-HN-AA$_1$-AA$_2$ . . . AA$_k$-OH include those where "k" is 1 to about 20. Especially preferred X-HN-AA$_1$-AA$_2$ . . . AA$_k$-OH include those wherein "k" is about 2 to about 10. More especially preferred X-HN-AA$_1$-AA$_2$ . . . AA$_k$-OHs include those where "k" is about 2 to about 5. "X" refers to a protecting group for the N-terminal amino acid or amino acid analog of X-HN-AA$_1$-AA$_2$ . . . AA$_k$-OH. Preferred protected amino acids for coupling include protected L-amino acids.

The preferred means of chemically coupling X-HN-AA$_1$-AA$_2$ . . . AA$_k$-OH is coupled to 2 include formation of a peptide bond by using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, X-HN-AA$_1$-AA$_2$ . . . AA$_k$-OH is coupled directly to 2. Preferred coupling reagents for one-step coupling of the include DCC with HOBt, EDC with HOBt, HBTU, TBTt, HBTU with HOBt or TBTU with HOBt. In two-step coupling, an activated ester or anhydride of the C-terminal carboxy group of X-HN-AA$_1$-AA$_2$ . . . AA$_k$-OH is formed prior to its coupling to 2.

X-HN-AA$_1$-AA$_2$ . . . AA$_k$-OH is protected to prevent side reactions and enhance correct coupling. Correct coupling requires that only the C-terminal carboxy group of X-HN-AA$_1$-AA$_2$ . . . AA$_k$-OH is chemically coupled to the free amino group of 2. In particular, the N-terminal amino group, and if necessary, the side-chain groups of X-HN-AA$_1$-AA$_2$ . . . AA$_k$-OH are protected by suitable protecting groups.

Where the synthesis of the desired peptidyl argininal is done by chemical coupling of a single X-HN-AA$_1$-AA$_2$ . . . AA$_k$-OH having on its N-terminal amino group a non-removable protecting group as "X" may be used. Suitable non-removable protecting groups include acyl groups or sulfonyl groups. Preferred non-removable protecting groups include acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl, and 1-camphorsulfonyl.

Where the synthesis of the desired peptidyl argininal is done by stepwise addition of multiple X-HN-AA$_1$-AA$_2$ . . . AA$_k$-OH, appropriate protecting groups as "X" and for the side chain function groups of the amino acids or amino acid analogs comprising X-HN-AA$_1$-AA$_2$ . . . AA$_k$-OH are selected which can be removed under non-adverse conditions. Non-adverse conditions means conditions of reaction or synthesis which do not substantially adversely affect the skeleton of this peptide and/or its amino acid components.

Suitable N-terminal amino protecting groups which can be removed under non-adverse conditions include: (a) aromatic urethane-type protecting groups which include benzyloxycarbonyl, 2-chlorobenzyloxycarbonyl, 9-fluorenylmethyloxycarbonyl, isonicotinyloxycarbonyl, and 4-methoxybenzyloxycarbonyl; (b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which include adamantyloxycarbonyl, cyclopentyloxycarbonyl, cyclohexyloxycarbonyl and isobornyloxycarbonyl. Preferred N-terminal protecting groups include benzyloxycarbonyl and t-butoxycarbonyl. Especially preferred protecting groups include t-butoxycarbonyl.

Suitable side-chain protecting groups which can also be removed under non-adverse conditions include: (a) for the side-chain amino group present of lysine, protecting groups include any of the groups mentioned above; (b) for the guanidino group of arginine, protecting groups include nitro, benzyloxycarbonyl, t-butoxycarbonyl, 2,2,5,7,8-pentamethylchroman-6-sulfonyl and 2,3,6-trimethyl-4-methoxyphenylsulfonyl; (c) for the hydroxyl group of serine, threonine or tyrosine, protecting groups include t-butyl, benzyl, p-methoxybenzyl, p-nitrobenzyl, p-chlorobenzyl, o-chlorobenzyl and 2,6-dichlorobenzyl; (d) for the carboxyl group of aspartic acid or glutamic acid, protecting groups include the methyl ester, ethyl ester, t-butyl ester and benzyl ester; (e) for the imidazole nitrogen of histidine, protecting groups include the benzyloxymethyl group; (f) for the phenolic hydroxyl group of tyrosine, protecting groups include tetrahydropyranyl, t-butyl, trityl, benzyl, chlorobenzyl, 4-bromobenzyl and 2,6-dichlorobenzyl; and (g) for the sulfhydryl group of cysteine, protecting groups include trityl, benzyl, 4-methoxybenzyl and 2,4,6-trimethylbenzyl. Protecting groups for the N-terminal amino group and side chain groups of amino acids and peptides such as those disclosed above are well known in the art. See Bodanszky, N., Peptide Chemistry, pp. 74–103, Springer-Verlag, New York (1988) and references cited therein.

It will be apparent to those skilled in the art that conditions for chemically removing protecting groups will vary. For example, certain protecting groups such as triphenylmethyl and 2-(4-biphenyl)-2-propyloxycarbonyl are very labile and can be cleaved under mild acid conditions. Other protecting groups, such as t-butoxycarbonyl, t-amyloxycarbonyl, adamantyloxycarbonyl, and 4-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl, 2-chlorobenzyloxycarbonyl, 4-nitrobenzyloxycarbonyl and isopropyloxycarbonyl, are even less labile and require stronger acids, such as hydrogen fluoride, hydrogen bromide, boron trifluoroacetate in trifluoroacetic acid or trifluoromethanesulfonic acid in trifluoroacetic acid, for their removal.

In X-HN-AA$_1$-AA$_2$ . . . AA$_k$-OH, the protecting groups (X) for the N-terminal amino group which are selected for use in the methods of the present invention can be chemically removed in the presence of the protecting groups on the side-chain functional groups of the amino acids, amino acid analogs, or combination of amino acids and amino acid analogs comprising X-HN-AA$_1$-AA$_2$ . . . AA$_k$-OH.

In selecting a particular N-terminal amino protecting group for use with certain side-chain protecting groups in the synthesis of peptidyl argininals, the following considerations may be determinative. An N-terminal amino protecting group should: (a) render the N-terminal amino group inert under the conditions employed in the coupling reaction, (b) be readily removable after the coupling reaction under conditions that will not remove side-chain protecting groups nor alter the structure of the peptide fragment, and (c) eliminate the possibility of racemization upon activation immediately prior to coupling. A side-chain protecting group should: (a) render the side-chain functional group inert under the conditions employed in the coupling reaction, (b) be stable under the conditions employed in removing the N-terminal amino protecting group, and (c) should be readily removable upon completion of the synthesis of peptidyl argininal under reaction conditions that will not alter its structure. The differential removal of a protecting group in the presence of other protecting groups is also well known in the art. See Fauchére J. -L. and Schwyzer, "Differential Protection and Selective Protection in Peptide Synthesis", The Peptides, Volume 3, pp. 203–252, Academic Press, New York (Edits. Gross, E. Meienhofer, J. 1981).

The selection of a protecting group, X, for the N-terminal amino amino acid or amino acid analog of X-HN-AA$_1$-AA$_2$ . . . AA$_k$-OH depends on what protecting group, R$_7$, is employed in the first intermediate used.

21

Where $R_7$ is nitro or benzyloxycarbonyl group, the preferred groups include t-butoxycarbonyl, t-amyloxycarbonyl, isobornyloxycarbonyl, adamantyloxycarbonyl, 4-methoxybenzyloxycarbony, or 2-(4-biphenyl)-2-propyloxycarbonyl. Especially preferred protecting groups include t-butoxycarbonyl. Alternatively, where $R_7$ is t-butoxycarbonyl or adamantyloxycarbonyl, the preferred protecting groups include benzyloxycarbonyl, isonicotinyloxycarbonyl, 2-chlorobenzyloxycarbonyl, 9-fluorenylmethoxycarbonyl or methylsulfonylethoxycarbonyl. Especially preferred protecting groups include benzyloxycarbonyl.

d. Chemically removing $R_7$ group.

As depicted in FIG. 3, the $R_7$ group of the third intermediate 3 is chemically removed to give a third intermediate 4.

Where the $R_7$ group is nitro or benzyloxycarbonyl, preferred means to chemically remove it from a third intermediate include treating the third intermediate with hydrogen gas in a liquid mixture comprised of catalyst, alcohol and acid. Especially preferred means include chemically removing such $R_7$ group by treatment with hydrogen gas on palladium in a liquid mixture comprised of ethanol and acetic acid.

Where the $R_7$ group is t-butoxycarbonyl or adamantyloxycarbonyl, preferred means to chemically remove it from a third intermediate include treating a third intermediate with a liquid mixture comprised of an acid and solvent. Especially preferred means include treatment with trifluoroacetic acid in a chlorinated hydrocarbon solvent. More especially preferred means include treatment with trifluoroacetic acid in dichloromethane at 0°–30° C., more preferably at 20°–25° C.

e. Hydrolyzing.

As depicted in FIG. 3, the fourth intermediate 4 is hydrolylzed to give the peptidyl aldehyde 5. Preferred means of hydrolyzing a fourth intermediate include treatment with aqueous acid. Preferred aqueous acids include HCl, $HPF_6$, methanesulfonic acid, perchloric acid, sulfuric acid, trifluoroacetic acid, trifluoromethanesulfonic acid, toluenesulfonic acid. Where a fourth intermediate contains either a beta ester of aspartic acid or gamma ester of glutamic acid, especially preferred acids include $HPF_6$. Where a fourth intermediate does not contain a beta ester of aspartic acid or gamma ester of glutamic acid, especially preferred acids include HCl and $HPF_6$.

To assist in understanding the present invention, the following examples follow, which include the results of a series of experiments. The following examples relating to this invention are illustrative an should not, of course, be construed as specifically limiting the invention. Moreover, such variations of the invention, now known or later developed, which would be within the purview of one skilled in the art are to be considered to fall within the scope of the present invention hereinafter claimed.

22

EXAMPLES

Example 1

Preparation of
N-alpha-t-butoxycarbonyl-$N^g$-nitro-L-arginine lactam

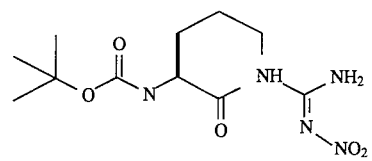

N-alpha-t-butoxycarbonyl-$N^g$-nitroargininine (2.00 g, 6.3 mmole) was dissolved in tetrahydrofuran (100 mL) by heating the solution to 50° C. The solution was allowed to cool to room temperature. N-methyl piperidine (0.84 mL, 6.9 mmole) was added, and the solution was cooled in an ice bath. Isobutylchloroformate (0.83 mL, 6.3 mmole) was added, and the reaction mixture was stirred at 0° C. for 6 hours. The reaction mixture was stirred for 18 hours while the ice in the dewar was allowed to melt overnight. The solvent was removed under vacuum. The crude product was dissolved in 20% ethyl acetate/dichloromethane (10 mL), and was purified by flash chromatography through a 3×5 cm column of silica gel using 20% ethyl acetate/dichloromethane as eluent. 125 mL of eluent was collected. The solvent was removed under vacuum to afford 1.39 g (74% crude yield) of the title compound as a white foam. $R_f$=0.44 (silica gel, 5% isopropanol in dichloromethane). Isobutanol was present as an impurity. This compound may be further purified by recrystallization from dichloromethane/hexanes or ethanol/water.

Example 2

Preparation of
N-alpha-t-butoxycarbonyl-$N^g$-nitro-L-argininal

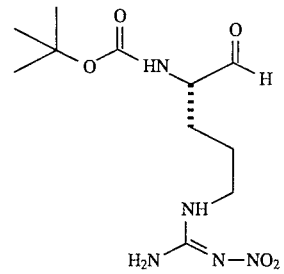

(a) Procedure 1.

To a stirred solution of $LiAlH_4$ in tetrahydrofuran (3.8 mL of a 1.0M solution, 3.8 mmole), cooled in an ice bath, was added dropwise ethyl acetate (0.43 mL, 3.8 mmole) in tetrahydrofuran (5 mL). The solution was stirred for 30 minutes at 0° C. to preform $LiAlH_2(OEt)_2$.

The solution of this $LiAlH_2(OEt)_2$ was added dropwise to a stirred solution of compound of Example 1 (0.92 g, 3.1 mmole) in tetrahydrofuran (5 mL). After 30 minutes, the reaction is quenched with 1.0N HCl/tetrahydrofuran (2 mL of a 1:1 mixture). 1.0N HCl (20 mL) was added, and the solution was extracted three times with ethyl acetate (20 mL each). The combined organic layers were washed with water (5 mL), saturated sodium bicarbonate (5 mL) and twice with brine(5 mL each), dried over anhydrous magnesium sulfate, filtered and the solvent was removed under vacuum to give 0.94 g (100% yield) of the title compound as an off-white solid.

(b) Procedure 2.

Alternatively, the title compound was made by the procedures which follow.

A 12 liter four-necked round bottom flask equipped with an overhead stirring apparatus was flame dried under a strong stream of nitrogen. After the flask had cooled, 120.0 g of N-alpha-t-butoxycarbonyl-N $^g$-nitro-L-arginine (376 mmole, 1 equivalent) was added under a blanket of nitrogen followed by the addition of 6 liters of anhydrous tetrahydrofuran (Aldrich sure-seal) via canula. The flask was then fitted with a thermometer and the resulting suspension was warmed to 50° C. with a heat gun while stirring. The reaction mixture was cooled to 5° C. with an ice bath and further cooled to −5° C. with an ice/acetone bath.

During the time it took for this solution to reach −5° C., 36.66 g of N-methyl-O-methylhydroxyamine hydrochloride (376 mmole, 1.0 equivalent) was weighed out in a 500 mL flask and suspended in 300 mL of dichloromethane. This suspension was sparged with nitrogen for 5 minutes, cooled to 0° C. and 46 mL of N-methylpiperidine (1.0 equivalent) was added via syringe under nitrogen. The mixture was sonicated briefly to insure complete dissolution/free base formation and recooled to 0° C. in an ice bath while still under nitrogen. The resulting solution of free base was used later.

When the above arginine solution had reached −5° C., 45 mL of N-methylpiperidine was added via syringe followed 5 minutes later by the addition of 46 mL of isobutyl chloroformate (0.95 equivalent) via syringe. The resulting solution was stirred for 15 minutes at −5° C. After this time, the free base solution of N-methyl-O-methyl hydroxylamine generated above was added via canula over about 15 minutes. Stirring was continued at −5° C. for another 1.5 hours at which time thin layer chromatography (silica gel, 1:10:90 acetic acid/methanol/dichloromethane) indicated that the reaction was complete. The reaction mixture was filtered while still cold, the salts washed with 400 mL of cold tetrahydrofuran and the filtrate concentrated under vacuum on a rotary evaporator to yield a yellow foam.

The crude intermediate was taken up in 300 mL of dichloromethane and applied to a column of silica gel (70–230 mesh, 7×50 cm). The column was first eluted with 2 liters of dichloromethane followed by 2 liters of 2% methanol in dichloromethane. This was followed by elution with 5% methanol in dichloromethane until all of the product had been eluted (the eluant was checked for UV activity and five one-liter fractions were collected once this UV activity was apparent). Fractions containing pure product were pooled and concentrated under vacuum and pumped on overnight to yield 120.1 g (88% yield) of N-alpha-t-butoxycarbonyl-N$^g$-nitro-L-arginine-(N-methyl, N-methoxyamide) as light yellow foam. This foam was taken up in 300 mL of dichloromethane, 300 mL of toluene, and the volatiles were once again removed under vacuum to remove any residual water or methanol.

120.1 g of N-alpha-t-butoxycarbonyl-N$^g$-nitro-L-arginine-(N-methyl, N-methoxyamide) (331.4 mmole) was taken up in 2.8 liters of dry (Aldrich sure-seal) tetrahydrofuran and transfered to a dry 5 liter 4-necked round bottom flask equipped with a mechanical stirrer and a low temperature thermometer. The solution was cooled to −70° C. with a dry ice/acetone bath and 300 mL of 1M LiAlH$_4$ in tetrahydrofuran was added by canula transfer directly from 100 mL Aldrich sure-seal bottles. An additional 50 mL of 1M LiAlH$_4$ in tetrahydrofuran was added via syringe (total 331 mL). During the additions, the reaction temperature was kept below −60° C. The reaction was stirred for 0.5 hours at −70° C., the cooling bath removed, and the reaction was slowly allowed to warm to 0° C. (about 2.5 hours). Between −30° C. and −20° C. a thick slurry resulted. When the reaction mixture obtained 0° C., a small aliquot was removed and partitioned between ethyl acetate/2M potassium bisulfate. The organic layer analyzed by thin layer chromatography (silica gel, ethyl acetate).

When the reaction was judged to be complete, it was cooled to −70° C. and 503 mL of 2M potassium bisulfate was added via dropping funnel at a slow enough rate to keep the reaction temperature below −30° C. The cooling bath was removed and the reaction mixture was allowed to come to 0° C. over the course of 2 hours at which time a white precipitate was filtered off. The solids were washed with 500 mL of cold tetrahydrofuran. The filtrate was concentrated under vacuum on a rotary evaporator until most of the tetrahydrofuran was removed and the remaining white sludge was mostly aqueous. The crude product was taken up in 1.5 liters of ethyl acetate and washed with 0.2 M HCl (2×200 mL). The HCl extracts were back-extracted with 400 mL of ethyl acetate and the organics were combined and extracted with saturated sodium bicarbonate (2×200 mL). The bicarbonate extracts were also back-extracted with 400 ml of ethyl acetate. The organics were then combined and washed with brine (200 mL) followed by drying over anhydrous sodium sulfate. The solution was filtered, concentrated under vacuum on a rotary evaporator and pumped on overnight to yield a white solid (89.0 g) of crude title compound. This was chromatographed on silica gel and eluted with a gradient of 0 to 10% methanol in dichloromethane. The pure fractions were combined and evaporated to yield the title compound as a white solid (75 g, 74%).

Example 3

Preparation of
N-alpha-t-butoxycarbonyl-N$^g$-nitro-L-argininal ethyl cyclol

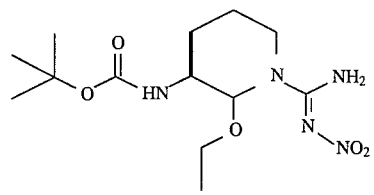

The compound of Example 2 (41.60 g, 0.137 mole) was dissolved in ethanol (200 mL) and concentrated HCl (1 mL) was added. After the reaction was complete by TLC (silica gel, 10% methanol in dichloromethane), the solvent was removed under vacuum. The crude product was purified by flash chromatography through a column of silica gel (230–400 mesh) using 0–10% ethyl acetate/dichloromethane as eluent. The combined fractions yielded 36.88 g (81%) of the title compound as pale yellow foam. R$_f$=0.62 (silica gel, 5% methanol in dichloromethane).

Example 4

Preparation of N$^g$-nitro-L-argininal ethyl cyclol, trifluoroacetate salt

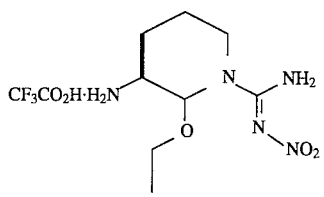

The compound of Example 3 (1.26 g) was treated with 50% trifluoroacetic acid/dichloromethane (10 mL) for 35 minutes. The solution was added dropwise to diethyl ether (100 mL) while swirling. The resulting precipitate was filtered and washed with diethyl ether. The light yellow powder was dried under vacuum to yield (1.20 g, 91%) of the title compound.

Example 5

Preparation of N$^g$-nitro-L-argininal ethyl cyclol, hydrochloride salt

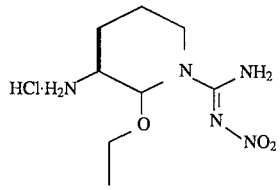

To a solution of the compound of Example 3 (35 g) in 500 mL of absolute ethanol at 0° C. was added slowly 500 mL of absolute ethanol saturated with HCl(g). This mixture was allowed to warm to 25° C. and checked by thin-layer chromatography. The appearance of a very polar product was the desired compound. Most of the HCl was removed with a stream of dry nitrogen and the resulting organic solvent was removed under vacuum. The resulting 33 g of the title compound as a yellow-white solid was used without furthur purification.

Example 6

Preparation of Boc-L-aspartyl-beta-(methyl ester)-L-proline-O-benzyl ester

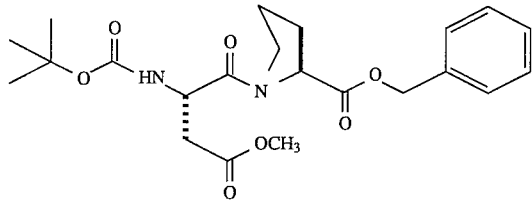

To a solution of isobutyl chloroformate (40.2 mL, 0.310 mole) and 1000 mL of ethyl acetate at 0° C. was added slowly N-methylmorpholine (51.2 mL, 0.465 mole). This mixture was stirred for 10 minutes with a mechanical stirrer. Boc-L-aspartic acid-beta-methyl ester (75 g, 0.283 mole) was added as a solid. The resulting solution was stirred for 15 minutes. Next, solid L-proline-O-benzyl ester hydrochloride salt (75 g, 0.310 mole) was added followed by the slow addition of N-methylmorpholine (44.4 mL, 0.403 mole). After 30 minutes, the ice bath was removed and the reaction was monitored by thin layer chromatography (silica gel, 5:95 methanol/dichloromethane). After about 2 hours, the reaction was completed, and the resulting organic phase was poured into 1 liter of water. The organic phase was separated and washed three times with 300 mL of 1N HCl, one time with 300 mL saturated sodium bicarbonate and one time with 100 mL of brine. The organic phase was dried over anhydrous magnesium sulfate, filtered and the solvent was removed under vacuum. The yield of the yellow oil of the title compound was 120.2 g (91%). R$_f$=0.76 (silica gel, 5:95 methanol/dichloromethane).

Example 7

N-(2-propylpentanoyl)-L-aspartyl-beta-(methyl ester)-L-proline-O-benzyl ester

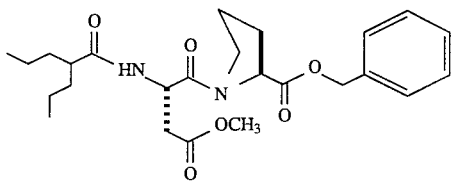

To a solution of the compound of Example 6 (112.6 g, 0.259 mole) and 400 mL of ethyl acetate at 0° C. was added with stirring 700 mL of ethyl acetate saturated with HCl (g). After about 1 hour, the reaction is completed by thin-layer chromatography (silica gel, 5:95 methanol/dichloromethane). After removing the solvent under vacuum, the resulting solid was suspended in 500 mL of ethyl acetate to give a solution of L-aspartyl-beta-(methyl ester)-L-proline-O-benzyl ester hydrochloride salt.

To a solution of isobutyl chloroformate (28.6 mL, 0.220) and 300 mL of ethyl acetate at 0° C. was added slowly N-methylmorpholine (31.3 mL, 0.285 mole). This mixture was stirred at 0° C. for 10 minutes and then 2-propylpentanoic acid (34.5 mL, 0.220 mole) was added. The resulting solution was stirred for 30 minutes and then added to the suspension of L-aspartyl-beta-(methyl ester)-L-proline-O-benzyl ester hydrochloride salt prepared above at 0° C. To this suspension was added slowly N-methylmorpholine (31.3 mL, 0.389 mole). The ice bath was removed after 30 minutes and the reaction mixture was allowed to warm to 25° C. After about 3 hours, the reaction was complete as determined by thin-layer chromatography (silica gel, 5:95 methanol/dichloromethane) and the resulting organic phase was poured into 1 liter of water. The organic phase was separated and washed with thee times with 1N HCl (3×100 mL), three time with saturated sodium bicarbonate (3×100 mL) and one time with brine (100 mL). The organic phase was dried over anhydrous magnesium sulfate, filtered and the solvent was removed under vacuum to give a residue.

The residue was chromatographed on silica gel (230–400 mesh, 14×70 cm column) and eluted with a gradient of 0 to 3% methanol in dichloromethane. The solvents were evaporated to yield of the 106.8 g (90%) of the title compound as a yellow oil. R$_f$=0.73 (silica gel, 5:95 methanol/dichloromethane).

Example 8

N-(2-propylpentanoyl)-L-aspartyl-beta-(methyl ester)-L-proline

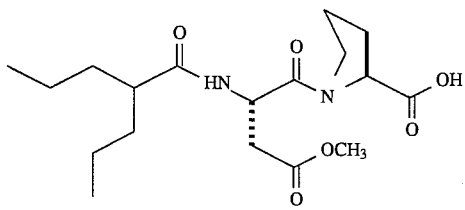

To a solution of the compound of Example 7 (111.6 g, 0.242 mole), 500 mL of methanol and 11 g of 10% palladium on carbon, wet with dichloromethane, was added hydrogen gas via a balloon. The reaction was stirred overnight at 25° C. The following day, the reaction was complete as determined by thin-layer chromatography (silica gel, 5:95 methanol/dichloromethane)). The solution was filtered through celite and and the celite was washed with dichloromethane (200 mL). The organic solvent was evaporated under vacuum. The resulting white solid was triturated with 300 mL of diethyl ether, filtered and dried to yield 47.3 g (58%) the title compound. $R_f$=0.23 (silica gel, 20:80 methanol/dichloromethane).

Example 9

Preparation of N-(2-propylpentanoyl)-L-aspartyl-beta-(methyl ester)-L-prolyl-$N^g$-nitro-L-argininal ethyl cyclol

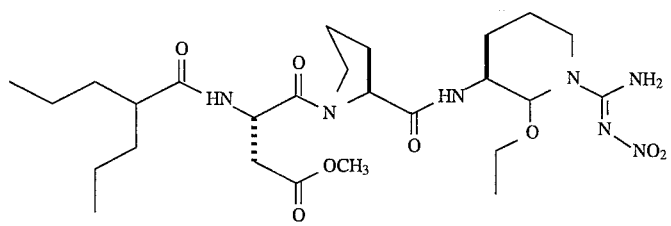

To a stirred solution of the compound of Example 8 (N-(2-propylpentanoyl)-L-aspartyl-beta-(methyl ester)-L-proline) (4.50 g, 12 mmole), HBTU (4.61 g, 12 mmole), and HOBt (1.64 g, 12 mmol) in acetonitrile (70 mL) was added 4-methylmorpholine (5.30 mL, 48 mmole). After 10 minutes, the compound of Example 4 ($N^g$-nitroargininal ethyl cyclol, trifluoroacetic acid salt) in acetonitrile (80 mL) was added. After 16 hours, the reaction mixture was concentrated, diluted with ethyl acetate (500 mL) and water (300 mL). The organic layers were combined and washed with 10% citric acid (3×300 mL), water (2×300 mL), saturated sodium bicarbonate (3×300 mL), and brine (2×100 mL). The solution was dried over anhydrous magnesium sulfate and the solvent was removed under vacuum. The residue was dissolved in ethyl acetate, and the product precipitated. The solution was filtered and air dried to give the title compound (4.39 g, 62% yield) as a yellow powder. Analytical HPLC gave $t_R$=16.1 minutes (20–60% CH$_3$CN/water containing 0.1% trifluoroacetic acid, 25 mm Vydac C-18 column). $R_f$=0.85 (silica gel, 10% methanol in dichloromethane).

Example 10

Preparation of N-(2-propylpentanoyl)-L-aspartyl-beta-(methyl ester)-L-prolyl-L-argininal ethyl cyclol, acetate salt

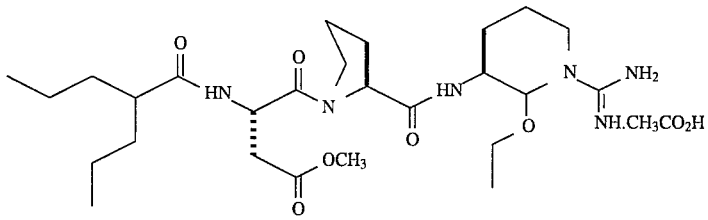

The compound of Example 9 (4.39 g, 8 mmole), acetic acid (1.72 mL, 30 mmole), and water (20 mL) in ethanol (75 mL) was hydrogenated over 10% palladium on carbon (0.44 g) for 72 hours at 45 psi. The reaction mixture was filtered through celite, washing with water. The solvent is removed under vacuum to yield 5.2 g (100% yield) of the title compound. Analytical HPLC gave $t_R$=13.3 minutes (20–60% CH$_3$CN/water containing 0.1% trifluoroacetic acid, 25 mm Vydac C-18 column.

Example 11

Preparation of
N-(2-propylpentanoyl)-L-aspartyl-beta-(methyl ester)-L-prolyl-L-argininal, trifluoroacetate salt

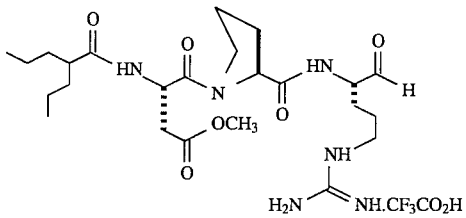

The compound of Example 10 (10.0 g, 17 mmole) was dissolved in 50% aqueous acetonitrile (200 mL) and cooled in an ice bath. HPF$_6$ (60% by weight, 150 mL) was added slowly, and the cooling bath was removed. After 30 minutes, the reaction mixture was recooled in an ice bath, and quenched with aqueous sodium acetate (1.25 L of a 2.5M solution) to pH 4, then filtered through a 2 micron filter. The filtrate was purified using the Biotage HPLC, Vydac column #3, C-18, 4×60 cm column, acid/0–40% water in acetonitrile containing 0.1% trifluoroacetic acid. The fractions were analyzed for purity by analytical HPLC (20–60% CH$_3$CN/water containing 0.1% trifluoroacetic acid, 25 mm Vydac C-18 column), combined and the acetonitrile was removed under reduced pressure. The remaining water was removed by lyophilization to give the title compound (4.26 g, 41% yield, 99% purity) as a white powder. 1.03 g (10%, 91% purity) was recovered from additional fractions. Fast atom bombardment mass spectrometry confirmed the theoretical molecular weight of 510.

Example 12

Preparation of
N-(2-propylpentanoyl)-L-aspartyl-L-prolyl-N$^g$-nitro-L-argininal ethyl cyclol

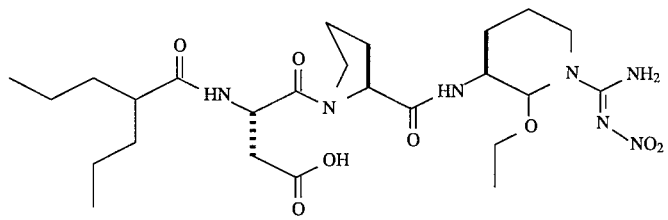

The compound of Example 9 (0.24 g, 0.41 mmole) was suspended in methanol (2 mL) and 1.0M LiOH (1.0 mL) was added dropwise. After 1 hour, the reaction mixture was diluted with water (10 mL) and washed with 2×3 mL ethyl acetate. The aqueous layer was adjusted with 1.0N HCl to pH 1.5, extracted with 3×5 mL ethyl acetate. The organic layers were combined and washed with 2×1 mL brine, and dried over anhydrous magnesium sulfate. The solvent was reduced to approximately 10 mL and upon sitting a solid crystallized out. The solid was filtered and air dried to give the title compound (110 mg, 47% yield) as an off-white crystals. Analytical HPLC gave t$_R$=13.3 minutes (20–60% CH$_3$CN/water containing 0.1% trifluoroacetic acid, 25 mm Vydac C-18 column).

Example 13

Preparation of
N-(2-propylpentanoyl)-L-aspartyl-L-prolyl-L-argininal ethyl cyclol, acetate salt

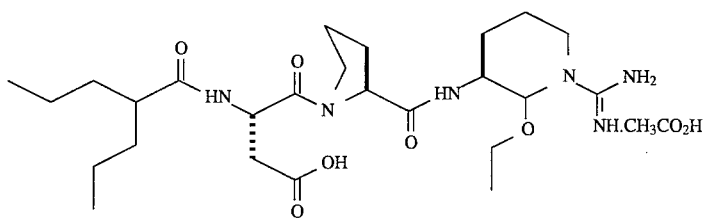

The compound of Example 12 (1.4 g, 2.2 mmole) in ethanol/acetic acid/water (4:1:1, 150 mL) was hydrogenated over 10% palladium on carbon (0.70 g) for 22.5 hours at 40 psi. The solution was filtered through celite, then the celite was washed with water. The solvent was removed under vacuum to yield 1.3 g (100% yield) of the title compound. Analytical HPLC gave t$_R$=11.2 minutes (20–60% CH$_3$CN/water containing 0.1% trifluoroacetic acid, 25 mm Vydac C-18 column).

Example 14

Preparation of
N-(2-propylpentanoyl)-L-aspartyl-L-prolyl-L-argininal,
trifluoroacetate salt

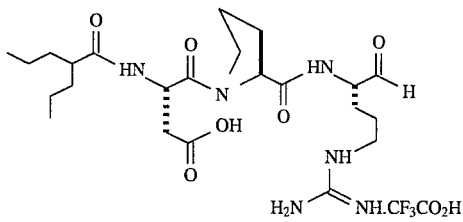

The compound of Example 13 (0.400 g, 0.68 mmole) was dissolved in water (30 mL) and cooled in an ice bath. Concentrated HCl (12N, 10 mL) was added and the cooling bath is removed. After 3.25 hours, the reaction mixture was quenched with aqueous sodium acetate (2.5M, 10 mL), then filtered through a 2 micron filter. The filtrate was purified by preparative HPLC (5×25 cm Vydac C-18 column, 0–40% acetonitrile/water containing 0.1% trifluoroacetic acid). Fractions were combined to give 120 mg (29% yield) of the title compound. Fast atom bombardment mass spectrometry confirmed the theoretical molecular weight of 496.

Example 15

Preparation of S-(t-butyl acetate)-L-cysteine

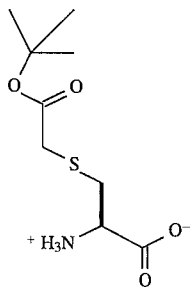

A 360 mL aqueous solution of commercially available (Aldrich) L-cysteine hydrochloride monohydrate (60.0 g, 341.7 mmole) and sodium hydroxide (27.33 g, 683.4 mmole), at room temperature, was treated with a solution of t-butyl bromoacetate (72.3 g, 370.6 mmole) in 130 mL of dioxane over 30 minutes. The reaction was stirred for 18 hours, during which time a thick precipitate formed. The solid was filtered off, washed with diethyl ether (100 mL) and dried under high vacuum at 40° C. to give 82.5 g (103.8% crude yield includes occluded inorganic salt) of the title compound.

Example 16

Preparation of N-Boc-S-(t-butyl acetate)-L-cysteine

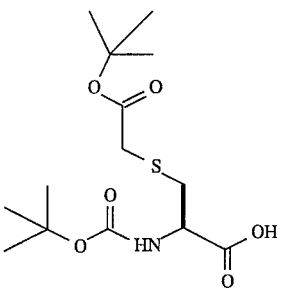

The compound of Example 15 (82.5 g, 341.7 mmole) and sodium bicarbonate (33.96 g, 404 mmole) were suspended in 600 mL of deionized water. A solution of di-t-butyl dicarbonate (80.88 g, 370 mmole) in 350 mL of dioxane was added and the slurry was stirred for 18 hours.

The slurry was extracted with diethyl ether (2×100 mL). The slurry was layered with ethyl acetate (200 mL) and acidified with 1N hydrochloric acid to pH 2 (pH papers). The resulting organic layer was saved and the remaining aqueous layer was further extracted with ethyl acetate (2×200 mL). The organic extracts were combined, washed with brine, dried with anhydrous magnesium sulfate and the solvent evaporated under vacuum to yield 84.3 g (74.6% yield) of the title compound as a clear oil. Thin layer chromatography analysis of the title compound showed a single spot with $R_f$=0.55, (silica; 90:10:2 dichloromethane/methanol/acetic acid).

Example 17

Preparation of N-Boc-S-(t-butyl acetate)-L-cysteine-L-proline-O-benzyl ester

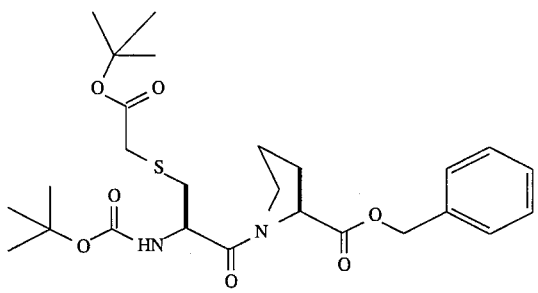

The compound of Example 16 (31.89 g, 95.06 mmole) and L-proline-O-benzyl ester hydrochloride (22.98 g, 95.06 mole) were suspended in 140 mL of acetonitrile and 120 mL of dimethylformamide at 0° C., then BOP (42.0 g, 95.06 mmole) and N-methylmorpholine (28.84 g, 285.18 mmole) were added. The ice bath was removed after 30 minutes and the reaction was stirred for 18 hours at room temperature. The reaction mixture was reduced in volume under vacuum at 25° C. to give an oil. The oil was dissolved in ethyl acetate (250 mL), then successively washed with 1N hydrochloric acid (1×50 mL), saturated sodium bicarbonate (1×50 mL) and brine (1×50 mL). The organic layer was dried with anhydrous magnesium sulfate and evaporated under vacuum to give crude product.

The crude product was purified by column chromatography on silica gel, eluting with 55:45 hexane/ethyl acetate to yield 27.91 g (57.9% yield) of the title compound as an oil. Thin layer chromatography analysis of the title compound showed a single spot with $R_f$=0.65 (silica, 3:2 ethyl acetate/hexane).

Example 18

Preparation of N-Boc-S-(t-butyl acetate)-L-cysteine sulfone-L-proline-O-benzyl ester

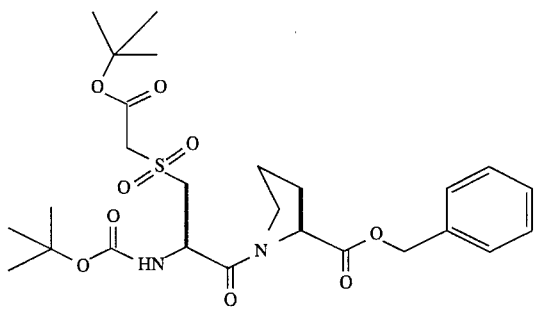

The compound of Example 17 (27.9 g, 55.07 mmole) was dissolved in 300 mL of glacial acetic acid, sodium perborate tetrahydrate (42.36 g, 275.35 mmole) was added and the mixture was heated to 55° C. After 2.5 hours at this temperature, the reaction mixture was diluted with 1 liter of brine, the aqueous layer was extracted with ethyl acetate (4×250 mL) and the combined organic extracts were dried with anhydrous magnesium sulfate. This solution was filtered and evaporated under vacuum, then repeatedly azeotroped with toluene (200 mL) under vacuum to remove acetic acid. The residual slurry was dissolved in ethyl acetate (200 mL), filtered and the filtrate evaporated to yield 29.7 g (100% yield) of the title compound as a white solid. Thin layer chromatography analysis of the title compound showed a single spot with $R_f$=0.60 (silica, 3:2 ethyl acetate/hexane).

Example 19

Preparation of N-(2-propylpentanoyl)-S-(t-butyl acetate)-L-cysteine sulfone-L-proline-O-benzyl ester

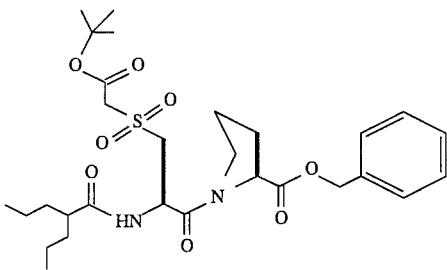

A solution of the compound of Example 18 (5.0 g, 9.28 mmole) in 105 mL of sieve-dried ethyl acetate was prepared. To this, 26 mL of 5.7N anhydrous hydrochloric acid/ethyl acetate (that had been generated in situ from acetyl chloride and methanol) was added. This mixture was stirred for several hours at room temperature until all starting material was consumed. The mixture was evaporated under vacuum and the resulting oil was dissolved in acetonitrile and then evaporated under vacuum. This was done three times.

The remaining oil was suspended in 35 mL of acetonitrile, cooled to ice bath temperature, then 2-propylpentanoic acid (1.60 g, 11.4 mmole), BOP (4.10 g, 9.28 mmole) and N-methylmorpholine (3.75 g, 37.1 mmole) were added. The reaction was removed from the ice bath after 30 minutes and allowed to stir at room temperature for 18 hours. The reaction mixture was reduced in volume under vacuum to an oil. The oil was taken up in 200 mL ethyl acetate and washed successively with 1N hydrochloric acid (1×50 mL), saturated sodium bicarbonate (1×50 mL) and brine (1×50 mL). After drying with anhydrous magnesium sulfate, the organic layer was evaporated under vacuum to give crude product.

The crude product was purified by column chromatography on silica gel, eluting with 3:2 hexane/ethyl acetate to yield 1.81 g (34.5% yield) of the title compound as a solid. Thin layer chromatography analysis of the title compound showed a single spot with $R_f$=0.50 (silica, 3:2 ethyl acetate/hexane).

Example 20

Preparation of N-(2-propylpentanoyl)-S-(t-butyl acetate)-L-cysteine sulfone-L-proline

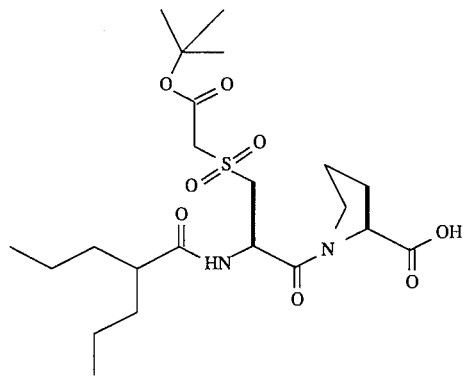

The compound of Example 19 (1.81 g, 3.2 mmole) was dissolved in tetrahydrofuran (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with anhydrous magnesium sulfate, filtered and evaporated under vacuum to give 1.30 g (yield 85.6%) of the title compound as a foamy solid. Thin layer chromatography analysis of the title compound showed a single spot with $R_f$=0.35 (silica, 90:10:2 dichloromethane/methanol/acetic acid).

Example 21

Preparation of N-(2-propylpentanoyl)-S-(t-butylacetate)-L-cysteine sulfone-L-proline-$N^g$-nitro-L-argininal ethyl cyclol

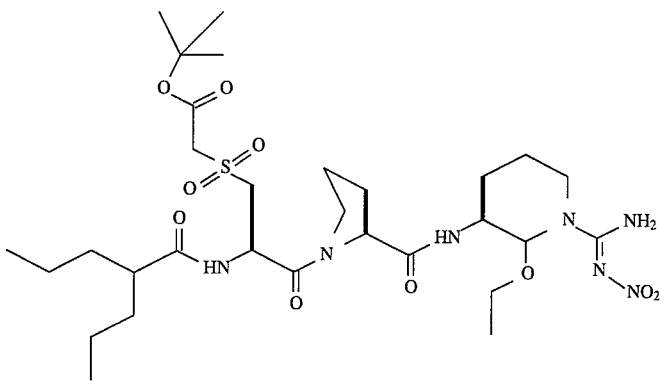

The compound of Example 5 (N$^g$-nitro-L-argininal ethyl cyclol, hydrochloride salt) (0.70 g, 2.6 mmole) was dissolved with stirring in 6 mL of dry dimethylformamide and 13 mL of dry acetonitrile. To this mixture was added N-methylmorpholine (1.4 mL, 13.1 mmole) followed by the compound of Example 20 (0.96 g, 1.9 mmole) HOBt (0.53 g, 3.9 mmole) and HBTU (1.5 g, 3.9 mmole). After 16 hours, the reaction mixture was diluted with 600 mL ethyl acetate and extracted with 150 mL each of water, 1M aqueous HCl, water, saturated aqueous sodium bicarbonate and brine. The organic phase was dried over anhydrous magnesium sulfate, filtered and the solvent removed under vacuum to give 1.3 g (95% yield) of the title compound as an off-white foam. $R_f$=0.50 (1:9 methanol/dichloromethane).

Example 22

Preparation of
N-(2-propylpentanoyl)-S-(t-butylacetate)-L-cysteine sulfone-L-proline-N$^g$-nitro-L-argininal ethyl cyclol, acetate salt

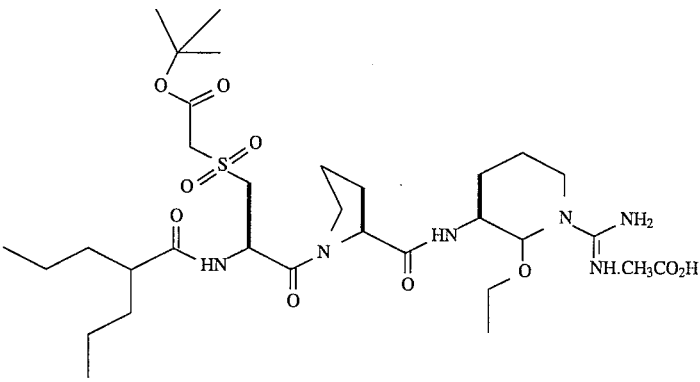

1.0 g of 10% palladium on carbon was placed in a 500 mL Parr bottle followed by 10 mL of water and 3.7 mL of glacial acetic acid was added. To this mixture was added, a solution of the compound of Example 21 (1.3 g, 1.85 mmole) in 100 mL of methanol. The mixture was then shaken under a hydrogen atmosphere at 40 psi for 3 days. The catalyst was then removed by filtration and the filtrate concentrated under vacuum to give an oil. The residue was purified by preparative HPLC (5×25 cm Vydac C-18 column, 10–40% aceto-nitrile/water containing 0.1% trifluoroacetic acid). Fractions were combined to give 0.7 g (58%) of the title compound.

Example 23

Preparation of
N-(2-propylpentanoyl)-S-(carboxymethyl)-L-cysteine sulfone-L-proline-N$^g$-nitro-L-argininal, trifluoroacetate salt

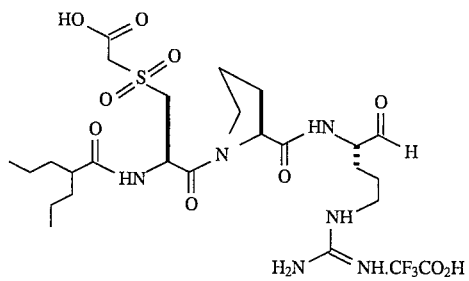

The compound of Example 22 (0.7 g, 1.1 mmole) was dissolved in 30 mL of 50:50 water/acetonitrile with stirring and cooled to 0° C. in an ice water bath. To this solution was slowly added 40 mL of a 60 wt % solution of HPF$_6$ in water. After 1 hour, analytical HPLC (20–60% CH$_3$CN/water containing 0.1% trifluoroacetic acid, 25 mm Vydac C-18 column) showed the reaction to be complete and pH of the reaction mixture was decreased to about pH=4 using 2.5M aqueous sodium actate. This mixture was filtered through a plug of celite and then was purified by preparative HPLC (1"×8" C18, 22 mL/min, 12–30%; acetonitrile/water containing 0.1%, trifluoroacetic acid) to give the title compound upon lyophilization of the pooled fractions. Fast atom bombardment mass spectrometry confirmed the theoretical molecular weight of 574.

Example 24

Preparation of
N-alpha-t-butoxycarbonyl-N$^g$-carbobenzyloxy-L-arginine

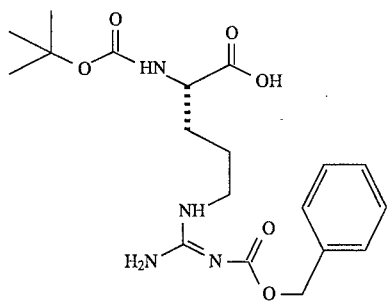

Alpha-N-tert-butyloxycarbonyl-L-arginine hydrochloride hydrate (82.1 g, 250 mmoles) is dissolved in 5.0N sodium hydroxide (240 mL) and cooled to −5° C. to 0° C. Under vigorous stirring benzyl chloroformate (143 mL, 1 mole) is added dropwise over a 55-minute period, while 5.0N sodium hydroxide (250 mL) is added to the solution at such a rate that the pH of the mixture is maintained at 13.2–13.5. Stirring is continued at 0° C. for 1 hour after addition of the chloroformate is complete. The reaction mixture is diluted with water (100 mL) and diethyl ether (500 mL). The aqueous layer is separated and extracted with diethyl ether (2×40 mL). The aqueous layer is acidified with 3N sulfuric acid to pH 3.0 (about 560 mL) and extracted with ethyl acetate (550 mL). The aqueous layer is extracted with ethyl acetate (250 mL). The combined ethyl acetate extracts are washed with water, dried over anhydrous magnesium sulfate and evaporated under reduced pressure. The precipitated product is triturated with diethyl ether, filtered, washed with diethyl ether and air-dried to give the title compound.

Example 25

Preparation of
N-alpha-t-butoxycarbonyl-N$^g$-carbobenzyloxy-L-arginine lactam

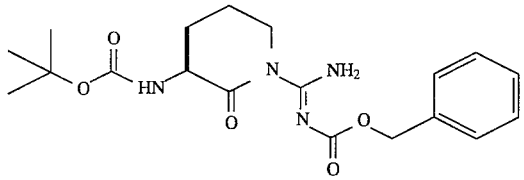

The compound from Example 24 (66.0 g, 162 mmole) is dissolved in tetrahydrofuran (230 mL) and the mixture is cooled to −10° C. in an ice-acetone bath. To the cold soution is added N-methylmorpholine (18.7 mL, 170 mmoles) followed by isobutyl chloroformate (22.5 mL, 170 mmoles). After stirring for 5 minutes, triethylamine (23.5 mL, 170 mmoles) is added. The reaction mixture is stirred for an additional hour at −10° C., then for one hour at room temperature. The reaction mixture is poured into ice water (1 L). The precipitated material is filtered, washed with cold water, dried under vacuum, and crystallized from ethyl acetate to give the title compound.

Example 26

Preparation of
N-alpha-t-butoxycarbonyl-N$^g$-carbobenzyloxy-L-argininal

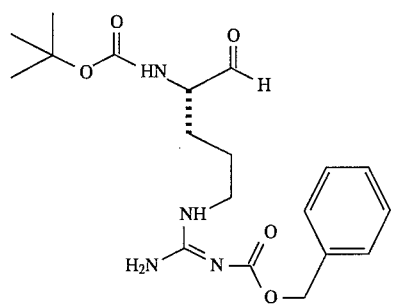

To a stirred solution of LiAlH$_4$ in tetrahydrofuran (4.8 mL of a 1.0M solution, 4.8 mmole), cooled in an ice bath, is added dropwise ethyl acetate (0.54 mL, 4.8 mmole) in tetrahydrofuran (5 mL). The solution is stirred for 30 minutes at 0° C. to preform LiAlH$_2$(OEt)$_2$.

The solution of this LiAlH$_2$(OEt)$_2$ is added dropwise to a stirred solution of the compound of Example 25 (1.50 g, 3.8 mmole) in tetrahydrofuran (10 mL). After 30 minutes, the reaction is quenched with 1.0N HCl/tetrahydrofuran (2.5 mL of a 1:1 mixture). 1.0N HCl (20 mL) is added, and the solution is extracted three times with ethyl acetate (3×20 mL). The combined organic layers are washed with water (5 mL), saturated sodium bicarbonate (5 mL) and twice with brine (2×5 mL). The extracts are dried over anhydrous magnesium sulfate, filtered and the solvent is removed under vacuum to give the title compound.

Example 27

Preparation of
N-alpha-t-butoxycarbonyl-N$^g$-carbobenzyloxy-L-argininal ethyl cyclol

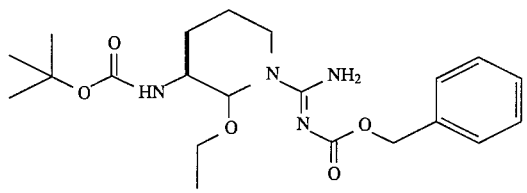

The compound of Example 26 (1.00 g, 2.5 mmole) is dissolved in ethanol (10 mL) and concentrated HCl (0.05 mL) is added. After the reaction is complete, the solvent is removed under vacuum. The crude product may be purified by flash chromatography through a column of silica gel (230–400 mesh). Removal of the solvents under vacuum from the combined fractions will yield the title compound.

Example 28

Preparation of $N^g$-carbobenzyloxy-L-argininal ethyl cyclol, trifluoroacetate salt

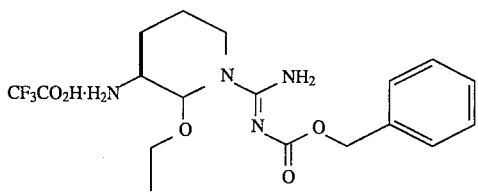

The compound of Example 27 (0.80 g) is treated with 50% trifluoroacetic acid/dichloromethane (8 mL) for 30 minutes. The solution is diluted with toluene, and the solvent is reduced under vacuum. The residue is again diluted with toluene, and the solvent is removed under vacuum to give the title compound. The resulting title compound is used without furthur purification.

Example 29

Preparation of $N^g$-carbobenzyloxy-L-argininal ethyl cyclol, hydrochloride salt

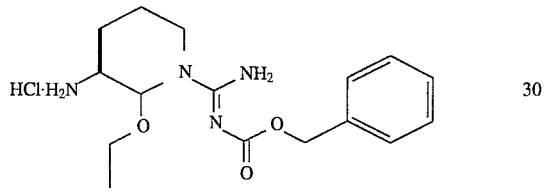

To a solution of the compound of Example 28 (3.5 g) in 50 mL of absolute ethanol at 0° C. is added slowly 50 mL of absolute ethanol saturated with HCl (g). This mixture is allowed to warm to 25° C. and checked by thin-layer chromatography. The HCl is removed with a stream of dry nitrogen and the remaining organic solvent is removed under vacuum to give the title compound. The title compound is used without further purification.

Example 30

Preparation of N-(2-propylpentanoyl)-L-aspartyl-beta-(methyl ester)-L-prolyl-$N^g$-carbobenzyloxy-L-argininal ethyl cyclol

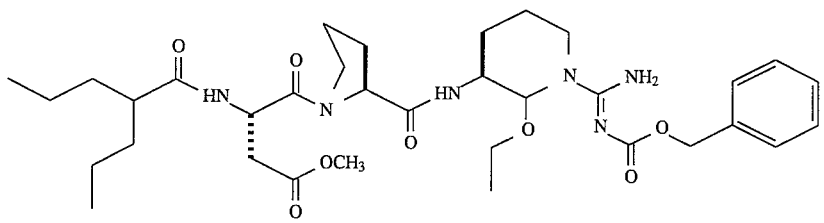

To a stirred solution of the compound of Example 8 (4.50 g, 12 mmole), HBTU (4.61 g, 12 mmole), and HOBt (1.64 g, 12 mmol) in acetonitrile (70 mL) is added 4-methylmorpholine (5.30 mL, 48 mmole). After 10 minutes, the compound of Example 29 (5.2 g, 12 mmole) in acetonitrile (80 mL) is added. After 16 hours, the reaction mixture is concentrated, diluted with ethyl acetate (500 mL) and water (300 mL). The organic layers are combined and washed three times with 10% citric acid (3×300 mL), two times with water (2×300 mL), three times with saturated sodium bicarbonate (3×300 mL), and two times with brine (2×100 mL). The solution is dried over anhydrous magnesium sulfate and the solvent is removed under vacuum. The crude product may be purified by flash chromatography through a column of silica gel (230–400 mesh). Upon removal of the solvents under vacuum the combined fractions will yield the title compound.

Example 31

Preparation of N-(2-propylpentanoyl)-L-aspartyl-beta-(methyl ester)-L-prolyl-L-argininal ethyl cyclol, acetate salt

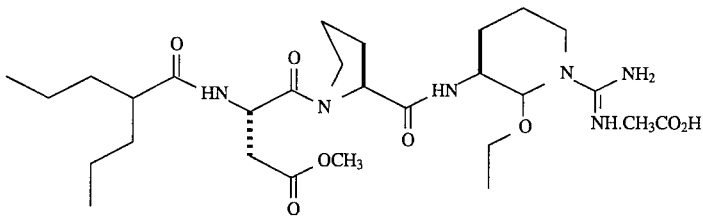

The compound of Example 30 (4.39 g, 8 mmole), acetic acid (1.72 mL, 30 mmole), and water (20 mL) in ethanol (75 mL) is hydrogenated over 10% palladium on carbon (0.44 g) for 5 hours at one atmosphere of hydrogen. The reaction mixture is filtered through celite, and the celite is washed with water. The solvent is removed under vacuum to yield the title compound.

Example 32

Preparation of N-(2-propylpentanoyl)-L-aspartyl-beta-(methyl ester)-L-prolyl-L-argininal, trifluoroacetate salt

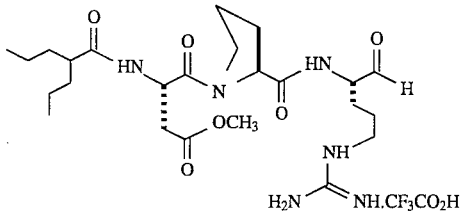

The compound of Example 31 (10.0 g, 17 mmole) is dissolved in 50% aqueous acetonitrile (200 mL) and cooled in an ice bath. $HPF_6$ (60% by weight, 150 mL) is added slowly, and the cooling bath is removed. After 30 minutes, the reaction mixture is recooled in an ice bath, and quenched with aqueous sodium acetate (1.25 L of a 2.5M solution) to pH 4, then is filtered through a 2 micron filter. The lilt rate is purified using the Blot age HPLC, Vydac column #3, C-18, 4×60 cm column, acid/0–40% water in acetonitrile containing 0.1% trifluoroacetic acid. The fractions are analyzed for purity by analytical HPLC (20–60% acetonitrile-water containing 0.1% trifluoroacetic acid, 25 mm Vydac C-18 column), combined and the acetonitrile is removed under reduced pressure. The remaining water is removed by lyophilization to give the title compound.

We claim:

1. A compound having the formula:

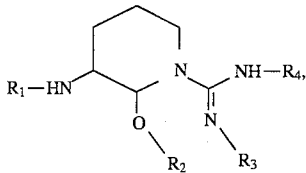

wherein $R_1$ is selected from the group consisting of hydrogen, benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

$R_2$ is selected from the group consisting of alkyl of 1 to about 12 carbon atoms, aralkyl of about 7 to about 15 carbon atoms, and alkyl of about 2 to about 12 carbon atoms substituted with a hydroxy, carbomethoxy or carboethoxy;

R3 is selected from the group consisting of nitro, benzyloxycarbonyl, t-butoxycarbonyl and adamantyloxycarbonyl; and $R_4$ is selected from the group consisting of hydrogen, alkyl of 1 to about 12 carbon atoms, aryl of about 6 to about 14 carbon atoms and aralkyl of about 7 to about 15 carbon atoms; or salts thereof.

2. A compound of claim 1, wherein $R_4$ is hydrogen, methyl, ethyl or propyl.

3. A compound of claim 2, wherein $R_4$ is hydrogen.

4. A compound of claim 3, where $R_3$ is nitro.

5. A compound of claim 4, wherein $R_2$ is alkyl of 1 to about 12 carbon atoms.

6. A compound of claim 5, wherein $R_2$ is methyl, ethyl, propyl or isopropyl.

7. A compound of claim 6, wherein $R_2$ is ethyl.

8. A compound of claim 7, wherein $R_1$ is hydrogen, 4-methoxybenzyloxycarbonyl, t-butoxycarbonyl, t-amyloxycarbonyl, isobornyloxycarbonyl, adamantyloxycarbonyl or 2-(4-biphenyl)-2-propyloxycarbonyl.

9. A compound of claim 8, wherein $R_1$ is hydrogen.

10. A compound of claim 8, wherein $R_1$ is t-butoxycarbonyl.

11. A compound of claim 3, where $R_3$ is benzyloxycarbonyl.

12. A compound of claim 11, wherein $R_2$ is alkyl of 1 to about 12 carbon atoms.

13. A compound of claim 12, wherein $R_2$ is methyl, ethyl, propyl or isopropyl.

14. A compound of claim 13, where $R_2$ is ethyl.

15. A compound of claim 14, wherein $R_1$ is hydrogen, 4-methoxybenzyloxycarbonyl, t-butoxycarbonyl, t-amyloxycarbonyl, isobornyloxycarbonyl, adamantyloxycarbonyl or 2-(4-biphenyl)-2-propyloxycarbonyl.

16. A compound of claim 15, wherein $R_1$ is hydrogen.

17. A compound of claim 15, wherein $R_1$ is t-butoxycarbonyl.

18. A compound of claim 3, where $R_3$ is t-butoxycarbonyl.

19. A compound of claim 18, wherein $R_2$ is alkyl of 1 to about 12 carbon atoms.

20. A compound of claim 19, wherein $R_2$ is methyl, ethyl, propyl or isopropyl.

21. A compound of claim 20, where $R_2$ is ethyl.

22. A compound of claim 21, wherein $R_1$ is hydrogen, benzyloxycarbonyl, isonicotinyloxycarbonyl or 2-chlorobenzyloxycarbonyl.

23. A compound of claim 22, wherein $R_1$ is hydrogen.

24. A compound of claim 23, wherein $R_1$ is benzyloxycarbonyl.

25. A compound of claim 1, selected from the group consisting of:
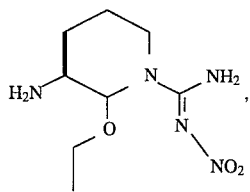
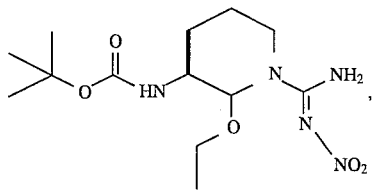
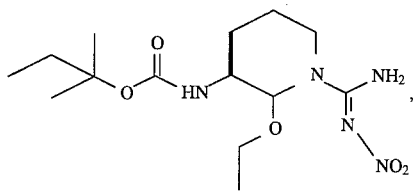
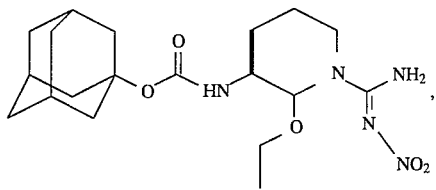
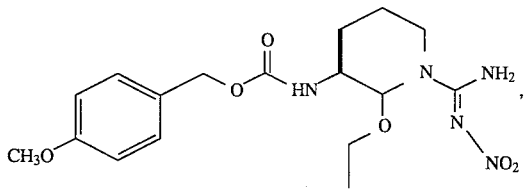
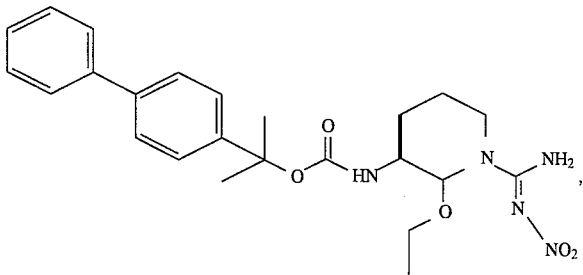
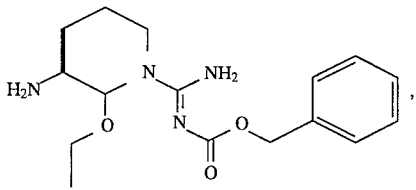

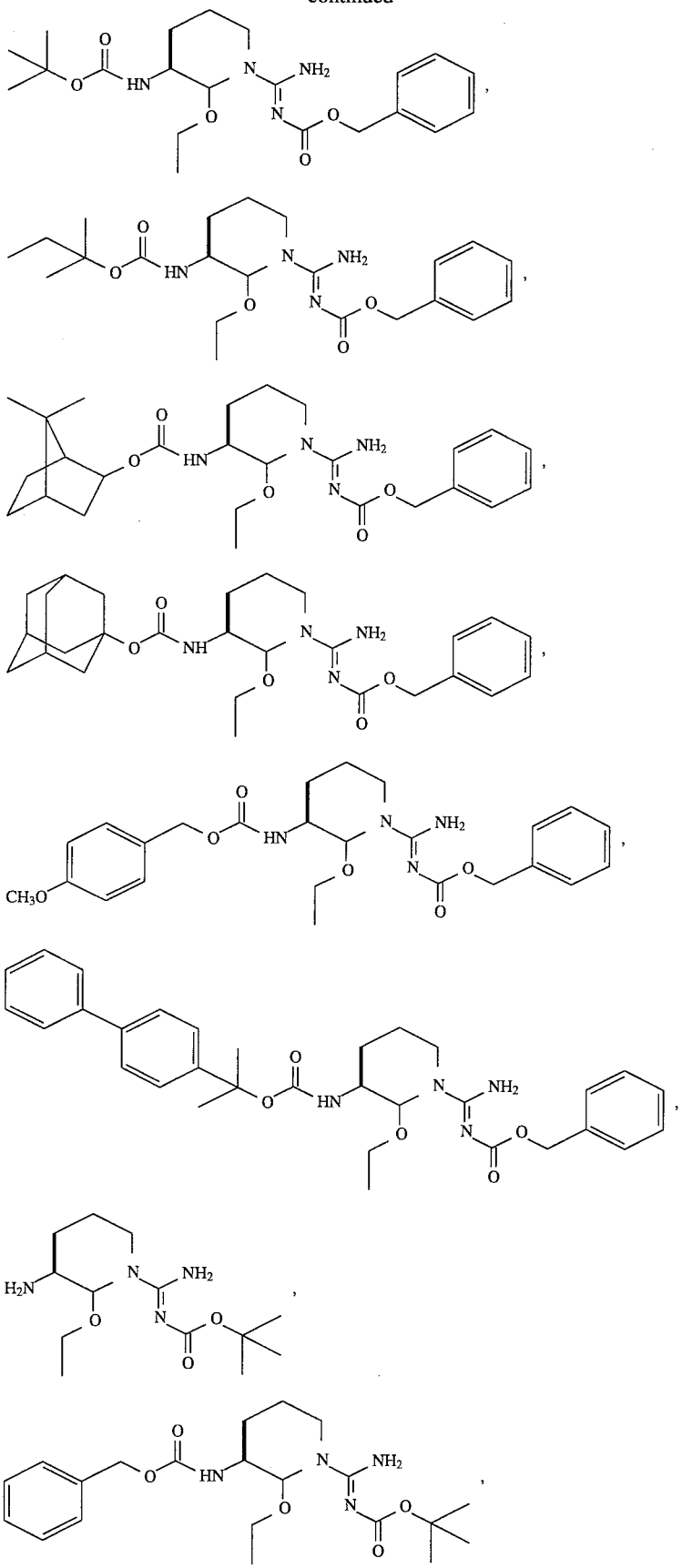

-continued

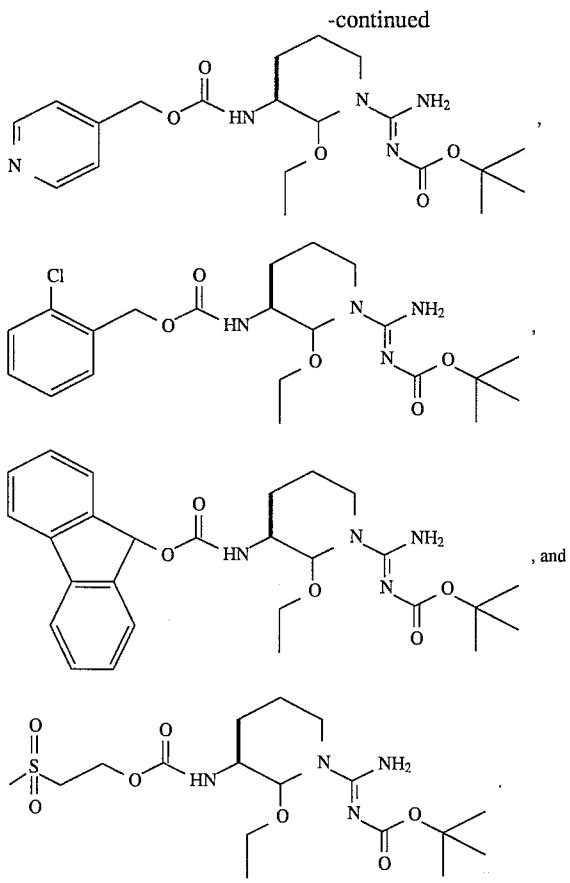

, and

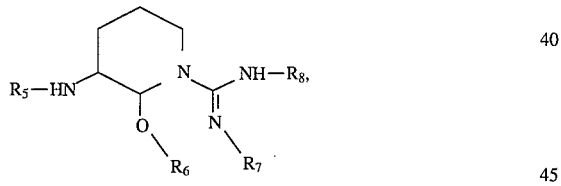

26. A method of making a peptidyl argininal comprising the steps of:

(a) reacting a first intermediate having the formula:

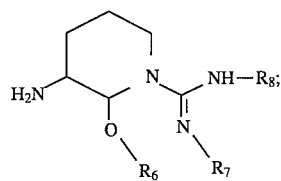

wherein

R$_5$ is selected from the group consisting of benzyloxycarbonyl, isonicotinyloxycarbonyl, 2-chlorobenzyloxycarbonyl, 4-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl and methylsulfonylethoxycarbonyl;

R$_6$ is selected from the group consisting of alkyl of 1 to about 12 carbon atoms, aralkyl of about 7 to about 15 carbon atoms, and alkyl of 2 to about 12 carbon atoms substituted with a hydroxy, carbomethoxy or carboethoxy;

R$_7$ is selected from the group consisting of nitro, benzyloxycarbonyl, t-butoxycarbonyl and adamantyloxycarbonyl; and R$_8$ is selected from the group consisting of hydrogen, alkyl of 1 to about 12 carbon atoms, aryl of about 6 to about 14 carbon atoms, and aralkyl of about 7 to about 15 carbon atoms; with a R$_5$ removing reagent which chemically removes the R$_5$ group from said first intermediate to give a second intermediate of the formula:

H$_2$N— (structure)

(b) chemically coupling to the second intermediate of step (a), a protected amino acid, a protected amino acid analog or a protected peptide of about 2 to about 30 amino acids, amino acid analogs, or a combination of amino acids and amino acid analogs, using a coupling reagent to give a third intermediate having the formula:

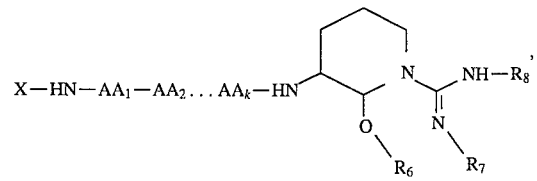

wherein
X is a protecting group,
k is an integer from 1 to 30, and
AA$_1$-AA$_2$...AA$_k$ is an amino acid, amino acid analog or peptide comprised of k amino acids, amino acid analogs or combination of amino acids and amino acid analogs;

(c) reacting the third intermediate with a R₇ removing reagent which chemically removes the R₇ group to give a fourth intermediate having the formula:

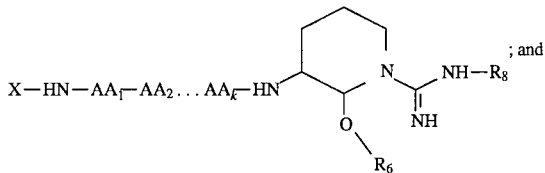

and (d) reacting the fourth intermediate with a hydrolyzing reagent which comprises an aqueous acid to chemically hydrolyze said fourth intermediate to give said peptidyl argininal.

27. A method of claim 26, wherein $R_8$ is hydrogen, methyl, ethyl or propyl.

28. A method of claim 27, wherein $R_8$ is hydrogen.

29. A method of claim 28, wherein $R_7$ is nitro.

30. A method of claim 29, wherein $R_6$ is alkyl of 1 to about 12 carbon atoms.

31. A method of claim 30, wherein $R_6$ is methyl, ethyl, propyl or isopropyl.

32. A method of claim 31, wherein $R_6$ is ethyl.

33. A method of claim 32, wherein $R_5$ is 4-methoxybenzyloxycarbonyl, t-butoxycarbonyl, t-amyloxycarbonyl, isobornyloxycarbonyl, adamantyloxycarbonyl and 2-(4-biphenyl)-2-propyloxycarbonyl.

34. A method of claim 33, wherein said $R_5$ removing reagent is a liquid mixture comprised of an acid and solvent.

35. A method of claim 34, wherein said acid is selected from the group consisting of HCl, trifluoroacetic acid and p-toluenesulfonic acid.

36. A method of claim 35, wherein said acid is HCl and said solvent is ethanol.

37. A method of claim 36, wherein said second intermediate is coupled to said $X-AA_1-AA_2 \ldots AA_k$-OH using a coupling reagent selected from the group consisting of DCC with HOBt, EDC with HOBt, HBTU, TBTU, HBTU with HOBt, and TBTU with HOBt.

38. A method of claim 37, wherein $R_7$ is chemically removed from said third intermediate by treating with hydrogen gas in a liquid mixture comprised of catalyst, alcohol and acid.

39. A method of claim 38, wherein said catalyst is palladium.

40. A method of claim 39, wherein said alcohol is ethanol and said acid is acetic acid.

41. A method of claim 40, wherein said hydrolyzing reagent is an aqueous acid selected from the group consisting of HCl, $HPF_6$, methane sulfonic acid, perchloric acid, sulfuric acid, trifluoroacetic acid, trifluoromethane sulfonic acid and toluene sulfonic acid.

42. A method of claim 41, wherein said aqueous acid is $HPF_6$ or HCl.

43. A method of claim 42, wherein X is selected from a group consisting of acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl.

44. A method of claim 43, wherein k is 2 to 10.

45. A method of claim 44, wherein k is 2 to 5.

46. A method of claim 28, wherein $R_7$ is benzyloxycarbonyl.

47. A method of claim 46, wherein $R_6$ is alkyl of 1 to about 12 carbon atoms.

48. A method of claim 47, wherein $R_6$ is methyl, ethyl, propyl or isopropyl.

49. A method of claim 48, wherein $R_6$ is ethyl.

50. A method of claim 49, wherein $R_5$ is 4-methoxybenzyloxycarbonyl, u-butoxycarbonyl, t-amyloxycarbonyl, isobornyloxycarbonyl, adamantyloxycarbonyl and 2-(4-biphenyl)-2-propyloxycarbonyl.

51. A method of claim 50, wherein said $R_5$ removing reagent is a liquid mixture comprised of an acid and solvent.

52. A method of claim 51, wherein said acid is selected from the group consisting of HCl, trifluoroacetic acid and p-toluenesulfonic acid.

53. A method of claim 52, wherein said acid is HCl and said solvent is ethanol.

54. A method of claim 53, wherein said second intermediate is coupled to said $X-AA_1-AA_2 \ldots AA_k$-OH using a coupling reagent selected from the group consisting of DCC with HOBt, EDC with HOBt, HBTU and TBTU.

55. A method to claim 54, wherein $R_7$ is chemically removed from said third intermediate by treating with hydrogen gas in a liquid mixture comprised of catalyst, alcohol and acid.

56. A method of claim 55, wherein said catalyst is palladium.

57. A method of claim 56, wherein said alcohol is ethanol and said acid is acetic acid.

58. A method of claim 57, wherein said hydrolyzing reagent is an aqueous acid selected from the group consisting of HCl, $HPF_6$, methane sulfonic acid, perchloric acid, sulfuric acid, trifluoroacetic acid, trifluoromethane sulfonic acid and toluene sulfonic acid.

59. A method of claim 58, wherein said aqueous acid is $HPF_6$ or HCl.

60. A method of claim 59, wherein X is selected from a group consisting of acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-napthalenesulfonyl and 1-camphorsulfonyl.

61. A method of claim 60, wherein k is 2 to 10.

62. A method of claim 61, wherein k is 2 to 5.

63. A method of claim 28, wherein $R_7$ is t-butoxycarbonyl.

64. A method of claim 63, wherein $R_6$ is alkyl of 1 to about 12 carbon atoms.

65. A method of claim 64, wherein $R_6$ is methyl, ethyl, propyl or isopropyl.

66. A method of claim 65, wherein $R_6$ is ethyl.

67. A method of claim 66, wherein $R_5$ is selected from the group consisting of benzyloxycarbonyl, isonicotinyloxycarbonyl and 2-chlorobenzyloxycarbonyl.

68. A method of claim 67, wherein said $R_5$ removing reagent is hydrogen gas or a source of hydrogen gas in a liquid mixture comprised of catalyst and solvent.

69. A method of claim 68, wherein said catalyst selected from the group consisting of platinum oxide or palladium.

70. A method of claim 69, wherein said catalyst is palladium.

71. A method of claim 70, wherein said solvent is comprised of ethanol and HCl.

72. A method of claim 70, wherein said second intermediate is coupled to said $X-AA_1-AA_2 \ldots AA_k$-OH using a coupling reagent selected from the group consisting of DCC with HOBt, EDC with HOBt, HBTU and TBTU.

73. A method of claim 72, wherein said $R_7$ removing reagent is a liquid mixture of an acid and solvent.

74. A method of claim 73, wherein acid is trifluoroacetic acid and solvent is dichloromethane.

75. A method of claim 74, wherein said hydrolyzing reagent is an aqueous acid selected from the group consisting of HCl, $HPF_6$, methane sulfonic acid, perchloric acid, sulfuric acid, trifluoroacetic acid, trifluoromethane sulfonic acid and toluene sulfonic acid.

76. A method of claim 75, wherein said aqueous acid is $HPF_6$ or HCl.

77. A method of claim 76, wherein X is selected from a group consisting of acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl.

78. A method of claim 77, wherein k is 2 to 10.

79. A method of claim 78, wherein k is 2 to 5.

* * * * *